(12) United States Patent  Gura

(10) Patent No.: US 10,933,183 B2
(45) Date of Patent: Mar. 2, 2021

(54) COMBINATION WEARABLE AND STATIONARY DIALYSIS SYSTEMS

(71) Applicant: Victor Gura, Beverly Hills, CA (US)

(72) Inventor: Victor Gura, Beverly Hills, CA (US)

(*) Notice: Subject to any disclaimer, the term of this patent is extended or adjusted under 35 U.S.C. 154(b) by 152 days.

(21) Appl. No.: 15/890,718

(22) Filed: Feb. 7, 2018

(65) Prior Publication Data

US 2018/0250461 A1    Sep. 6, 2018

Related U.S. Application Data

(60) Provisional application No. 62/456,056, filed on Feb. 7, 2017.

(51) Int. Cl.
*A61M 1/16* (2006.01)
*A61M 1/36* (2006.01)
*A61M 1/26* (2006.01)
*A61K 31/727* (2006.01)
(Continued)

(52) U.S. Cl.
CPC ......... *A61M 1/1633* (2014.02); *A61K 31/727* (2013.01); *A61K 33/00* (2013.01); *A61K 33/06* (2013.01); *A61M 1/1654* (2013.01); *A61M 1/1696* (2013.01); *A61M 1/267* (2014.02); *A61M 1/3672* (2013.01); *A61M 1/3679* (2013.01); *A61M 1/1649* (2014.02); *A61M 2205/3324* (2013.01); *A61M 2205/75* (2013.01); *A61M 2205/8206* (2013.01); *A61M 2209/088* (2013.01)

(58) Field of Classification Search
None
See application file for complete search history.

(56) References Cited

U.S. PATENT DOCUMENTS

| 5,171,216 A * | 12/1992 | Dasse | A61M 25/007 |
| | | | 604/175 |
| 2004/0068219 A1* | 4/2004 | Summerton | A61M 1/3413 |
| | | | 604/5.01 |
| 2009/0120864 A1 | 5/2009 | Fulkerson | |

(Continued)

FOREIGN PATENT DOCUMENTS

| CN | 110520170 A | 11/2019 |
| IN | 201917035687 A | 11/2019 |

(Continued)

OTHER PUBLICATIONS

"International Application Serial No. PCT US2018 017234, International Search Report dated Apr. 19, 2018", 3 pgs.

(Continued)

*Primary Examiner* — Hayden Brewster
(74) *Attorney, Agent, or Firm* — Schwegman Lundberg & Woessner, P.A.

(57) ABSTRACT

A system for hemodialysis can include a first dialysis system and a second dialysis system configured to be used in alternate fashion to provide hemodialysis for a patient, wherein the first dialysis system is configured to be worn by the patient, and wherein the second dialysis system is configured to be positioned on a support independent of the patient. The first dialysis system can be configured to be coupled to a belt worn by the patient around a waist of the patient during its operation. The second dialysis system can configured to be coupled to a stationary support during its operation.

15 Claims, 10 Drawing Sheets

(51) Int. Cl.
    *A61K 33/06*    (2006.01)
    *A61K 33/00*    (2006.01)

(56) References Cited

U.S. PATENT DOCUMENTS

| | | |
|---|---|---|
| 2013/0213890 A1 | 8/2013 | Kelly et al. |
| 2014/0276376 A1 | 9/2014 | Rohde et al. |
| 2015/0144539 A1 | 5/2015 | Pudil et al. |
| 2015/0314056 A1 | 11/2015 | Giordano et al. |

FOREIGN PATENT DOCUMENTS

| | | |
|---|---|---|
| WO | WO-2009083011 A2 | 7/2009 |
| WO | WO-2012067585 A1 | 5/2012 |
| WO | 2018148287 | 8/2018 |

OTHER PUBLICATIONS

"International Application Serial No. PCT US2018 017234, Written Opinion mailed Apr. 19, 2018", 7 pgs.

"International Application Serial No. PCT/US2018/017234, International Preliminary Report on Patentability dated Aug. 22, 2019", 9 pgs.

"European Application Serial No. 18750598.7, Extended European Search Report dated Jan. 16, 2020", 8 pgs.

"European Application Serial No. 18750598.7, Response filed Jul. 13, 2020 to Extended European Search Report dated Jan. 16, 2020", 23 pgs.

\* cited by examiner

COMBINATION WEARABLE AND STATIONARY DIALYSIS SYSTEMS

CROSS-REFERENCE TO RELATED APPLICATIONS

This application claims the benefit of U.S. Provisional Application No. 62/456,056, filed Feb. 7, 2017, which application is incorporated herein by reference.

BACKGROUND OF THE INVENTION

Hemodialysis can be a renal replacement therapy used by patients who have end stage renal disease (ESRD). These patients can no longer rely upon their kidney to provide desired removal of waste from the blood. Hemodialysis can involve removal of toxins from a patient's blood using a dialyzer, where the toxins diffuse across a semipermeable membrane in the dialyzer to a dialysate solution due to a concentration gradient across the membrane.

BRIEF SUMMARY OF THE INVENTION

Additional aspects and advantages of the present disclosure will become readily apparent to those skilled in this art from the following detailed description, wherein only exemplary embodiments of the present disclosure are shown and described, simply by way of illustration of the several modes or best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

A system for hemodialysis comprises: a first dialysis system and a second dialysis system configured to be used in combination, in an alternating fashion, over a combined cycle, to provide hemodialysis for a patient, wherein the first dialysis system is configured to be worn by the patient during a first portion of the combined cycle, and wherein the second dialysis system is configured to be positioned on a support independent of the patient during a second portion of the combined cycle.

Optionally, in any embodiment, the first dialysis system comprises a dialyzer; a blood circuit configured to receive blood from the patient and circulate the blood through the dialyzer; and a dialysate circuit, excluding a urea converter, configured to circulate dialysate through the dialyzer to receive toxins removed from the blood, wherein the dialysate circuit comprises a filter with a sorbent material consisting of or comprising activated carbon.

In some embodiments, the second dialysis system comprises a dialyzer; a blood circuit configured to receive blood from the patient and circulate the blood through the dialyzer to remove toxins from the blood; and a sterile dialysate circuit configured to circulate dialysate through the dialyzer to receive the toxins removed from the blood, wherein the dialysate circuit comprises a urea converter configured to remove urea from the dialysate.

Optionally, in any embodiment, the system for hemodialysis comprises a side-to-side pulsatile pump operably coupled to the blood circuit and the dialysate circuit to simultaneously drive the blood and the dialysate therethrough.

In some embodiments, the first dialysis system is coupled to a belt worn by the patient, around a waist of the patient during operation, untethered, to allow the patient to move unconstrained. In some embodiments, the second dialysis system is configured to be coupled to a stationary support during operation. In some embodiments, the second dialysis system removes additional toxins from the blood, not accounted for by the first dialysis system and can be removed in a shorter period of time than is required for the total time of the combined cycle.

Optionally, in any embodiment, the first dialysis system is powered by a battery; a rechargeable battery; or a combination thereof.

Optionally, in any embodiment, the second dialysis system is powered by a battery; a rechargeable battery; a power cord for an electrical outlet; or a combination thereof.

Provided herein is a system for hemodialysis, comprising a first dialysis system and a second dialysis system used in a combined fashion, over a combined cycle, to provide hemodialysis for a patient, wherein the first dialysis system is coupled to a belt worn by the patient during operation for at least a first portion of the combined cycle, untethered, to allow the patient to move unconstrained, wherein the second dialysis system is configurable to be positioned on a support independent of the patient during a second portion of the combined cycle; and wherein components of the second dialysis system are releasably coupled to the first dialysis system to create a tethered system.

In some embodiments, the first dialysis system comprises: a dialyzer comprising semi-porous membranes; a blood circuit configured to receive blood from the patient and circulate the blood through the dialyzer; a sterile dialysate circuit, excluding a urea converter, operable to circulate dialysate through the dialyzer to receive toxins removed from the blood, wherein the dialysate circuit comprises a filter with a sorbent consisting of activated carbon; and a side-to-side pulsatile pump operably coupled to the blood and dialysate circuits, wherein actuation of the side-to-side pump advances the blood and the dialysate, respectively therethrough.

In some embodiments, the second dialysis system comprises a urea converter configured to remove urea from the dialysate during the second portion of the cycle.

Optionally, in any embodiment, the first dialysis system comprises: a battery; a rechargeable battery; or a combination thereof.

Optionally, in any embodiment, the second dialysis system further comprises; a battery; a rechargeable battery; a power cord for attachment to an external power source, or a combination thereof.

In some embodiments of a system for hemodialysis described herein, the system further comprises: an ultrafiltrate collector operably coupled to the dialysate circuit after the pump to continuously remove excess fluid therefrom; a blood thinner reservoir operably coupled to the blood circuit to supply blood thinner thereto; one or more electrolyte reservoirs operably coupled to the dialysate circuit to supplement the dialysate flow with electrolytes or a gas removal component operably coupled to the dialysate circuit after the urea converter to continuously remove gas produced in the dialysate regeneration process.

In some embodiments, the blood thinner reservoir comprises heparin or a blood thinner.

Optionally, in any embodiment, the one or more electrolyte reservoirs comprise: sodium bicarbonate; magnesium; or calcium.

Optionally, in any embodiment of a system for hemodialysis described herein, the system further comprises an optional pH sensor to test for a change in pH caused by ammonia in the blood circuit.

Optionally, in any embodiment, the urea converter further comprises: one or more sorbent-containing cartridges; or one or more sorbent-containing cartridges comprising more than one distinct portion, wherein the one or more sorbent-containing cartridges or one or more sorbent-containing distinct portions each comprise one or more sorbent materials.

Optionally, in any embodiment, a sorbent material in the one or more sorbent-containing cartridges comprises: zirconium phosphate; hydrous zirconium oxide; metals or alloys containing zirconium; an organic and/or inorganic compound comprising zirconium; minerals comprising zirconium; or urease.

Optionally, in any embodiment of a system for hemodialysis described herein, the system further comprises: a blood tubing and a dialysate tubing comprising a plurality of filaments embedded therewithin; or a dual lumen catheter having a first lumen for blood and a second lumen for dialysate, comprising a plurality of filaments embedded therewithin; wherein the filaments extend along one or more portions of the blood or dialysate tubing or dual lumen; or extend along an entire length of the blood or dialysate tubing, wherein the filaments provide an increase in rigidity to reduce or prevent kinking.

Optionally, in any embodiment disclosed herein, the filaments are comprised of an electrically conductive material capable of relaying a signal to a control unit when the blood tubing, the dialysate tubing or the dual lumen catheter becomes kinked. Optionally, in any embodiment disclosed herein, the filaments comprise copper or nitinol.

Optionally, in any embodiment of a system for hemodialysis described herein, the first dialysis system is configured for about 8 hours of continuous use; about 10 hours of continuous use; about 12 hours of continuous use; about 14 hours of continuous use; or about 16 hours of continuous use; during the first portion of the combined cycle within a 24 hour period.

Optionally, in any embodiment of a system for hemodialysis described herein, the second dialysis system is configured for about 8 hours of continuous use; about 10 hours of continuous use; about 12 hours of continuous use; about 14 hours of continuous use; or about 16 hours of continuous use, during the second portion of the combined cycle within a 24 hour period.

Provided herein is a method of hemodialysis comprising removing first toxins from a first blood flow received from a patient using a first dialysate, wherein removing the first toxins comprises circulating the first blood flow and the first dialysate through a first dialysis system not comprising a urea converter for a first duration of time, the first dialysis system being configured to be worn by a patient; removing second toxins from a second blood flow received from the patient using a second dialysate, wherein removing the second toxins comprises circulating the second blood flow and the second dialysate through a second dialysis system comprising a urea converter for a second duration of time, the second dialysis system being configured to be positioned on a support independent of the patient, wherein circulating the first blood flow and the first dialysate through the first dialysis system and circulating the second blood flow and the second dialysate through the second dialysis system are performed in alternating fashion for a combined duration of time comprising the first duration of time and the second duration of time.

Optionally, in any embodiment disclosed herein, circulating the first blood flow and the first dialysate through the first dialysis system comprises flowing the first dialysate through a sorbent material of a first dialysis circuit, and wherein the sorbent material of the first dialysis circuit consists of or comprises activated carbon.

In any of the embodiments described herein, flowing the second blood flow and second dialysate through the second dialysis system comprises removing urea from the second dialysate.

Optionally, in any embodiment disclosed herein, the first dialysis system is configured to be coupled to a belt worn by the patient around a waist of the patient during operation for the first duration of time, untethered, to allow the patient to move unconstrained.

In some embodiments, the second dialysis system is configured to be coupled to a stationary support during operation for the second duration of time such that the patient is tethered to the support.

Optionally, in any embodiment disclosed herein, the second dialysis system is releasably coupled to the first dialysis system to create a tethered system.

Provided herein is a system for hemodialysis comprising a dual lumen catheter comprising a plurality of filaments embedded therewithin, the dual lumen catheter comprising a first end configured to be inserted within a superior vena cava or a subclavian vein of a patient, and a second end configured to extend from a waist of the patient; a first dialysis system and a second dialysis system configured to be coupled to the dual lumen catheter, the first dialysis system and a second dialysis system being configured to be used in alternate fashion over first and second combined durations of time to provide hemodialysis for the patient, wherein the first dialysis system is operably coupled to and worn by the patient for the first duration of time, and wherein the second dialysis system is operably coupled to the patient and positioned on a support independent of the patient for the second duration of time.

In some embodiments, the first dialysis system comprises a dialyzer; a blood circuit configured to receive blood from the patient and circulate the blood through the dialyzer; a dialysate circuit, excluding a urea converter, configured to circulate dialysate through the dialyzer to receive the toxins removed from the blood, wherein a sorbent material of the dialysate circuit consists or comprises of activated carbon; and a side-to-side pulsatile pump operably coupled to the blood and dialysate circuits, wherein actuation of the side-to-side pump advances the blood and the dialysate, respectively therethrough.

In some embodiments, the second dialysis system comprises a dialyzer; a blood circuit configured to receive blood from the patient and circulate the blood through the dialyzer to remove toxins from the blood; a sterile dialysate circuit configured to circulate dialysate through the dialyzer to receive the toxins removed from the blood, wherein the dialysate circuit comprises a urea converter configured to remove urea from the dialysate and a side-to-side pulsatile pump operably coupled to the blood and dialysate circuits, wherein actuation of the side-to-side pump advances the blood and the dialysate, respectively therethrough.

In some embodiments, the first dialysis system is disposed on a belt worn by the patient around a waist of the patient during operation, untethered, to allow the patient to move unconstrained.

Optionally, in any embodiment disclosed herein, the second dialysis system is disposed on the support during operation, such that the patient is tethered to the support.

Provided herein is a system for hemodialysis comprising a dual lumen catheter comprising a plurality of filaments embedded therewithin, the dual lumen catheter comprising a first end operably insertable within a superior vena cava or a subclavian vein of a patient, and a second end operably extendable from a waist of the patient; a first dialysis system and a second dialysis system operably coupled to the dual lumen catheter, the first dialysis system and the second dialysis system being configured to be used in alternating fashion over a first duration of time and a second duration of time respectively, combined to provide hemodialysis for a patient, wherein the first dialysis system is operably coupled to a belt and worn by the patient, for the first duration of time, wherein the second dialysis system is operably coupled to the patient and positioned on a support independent of the patient; and wherein components of the second dialysis system are releasably attachable to the first dialysis system to create a tethered system.

In some embodiments, the first dialysis system comprises a dialyzer; a blood circuit configured to receive blood from the patient and circulate the blood through the dialyzer; a sterile dialysate circuit excluding a urea converter, to circulate dialysate through the dialyzer to receive the toxins removed from the blood, wherein a sorbent material of the dialysate circuit consists of or comprises activated carbon; and a side-to-side pulsatile pump operably coupled to the blood and dialysate circuits, wherein actuation of the side-to-side pump advances the blood and the dialysate, respectively therethrough.

Optionally, in any embodiment disclosed herein, the second dialysis system comprises a sterile dialysate circuit comprising a urea converter configured to remove urea from the dialysate and a side-to-side pulsatile pump operably coupled to the blood and dialysate circuits, wherein actuation of the side-to-side pump advances the blood and the dialysate, respectively therethrough.

In some embodiments, the first dialysis system further comprises a battery; a rechargeable battery; or a combination thereof.

Optionally, in any embodiment disclosed herein, the second dialysis system further comprises a battery; a rechargeable battery; a power cord for attachment to an external power source; or a combination thereof.

Optionally, in any embodiment disclosed herein, components of the second dialysis system are releasably attachable to the first dialysis system, and the second dialysis system comprises a power cord for attachment to an external power source and is configurable to recharge the battery of the first dialysis system.

Optionally, in any embodiment disclosed herein, the system further comprises an ultrafiltrate collector operably coupled to the dialysate circuit to continuously remove excess fluid therefrom; a blood thinner reservoir operably coupled to the blood circuit to supply blood thinner thereto; optional one or more electrolyte reservoirs operatively coupled to the dialysate circuit to supplement the dialysate with electrolytes; an optional pH sensor in the blood circuit to test for a change in pH caused by ammonia in the blood circuit; or an optional gas removal component operably coupled to the dialysate circuit after the urea converter, to continuously remove gas produced in the dialysate regeneration process.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
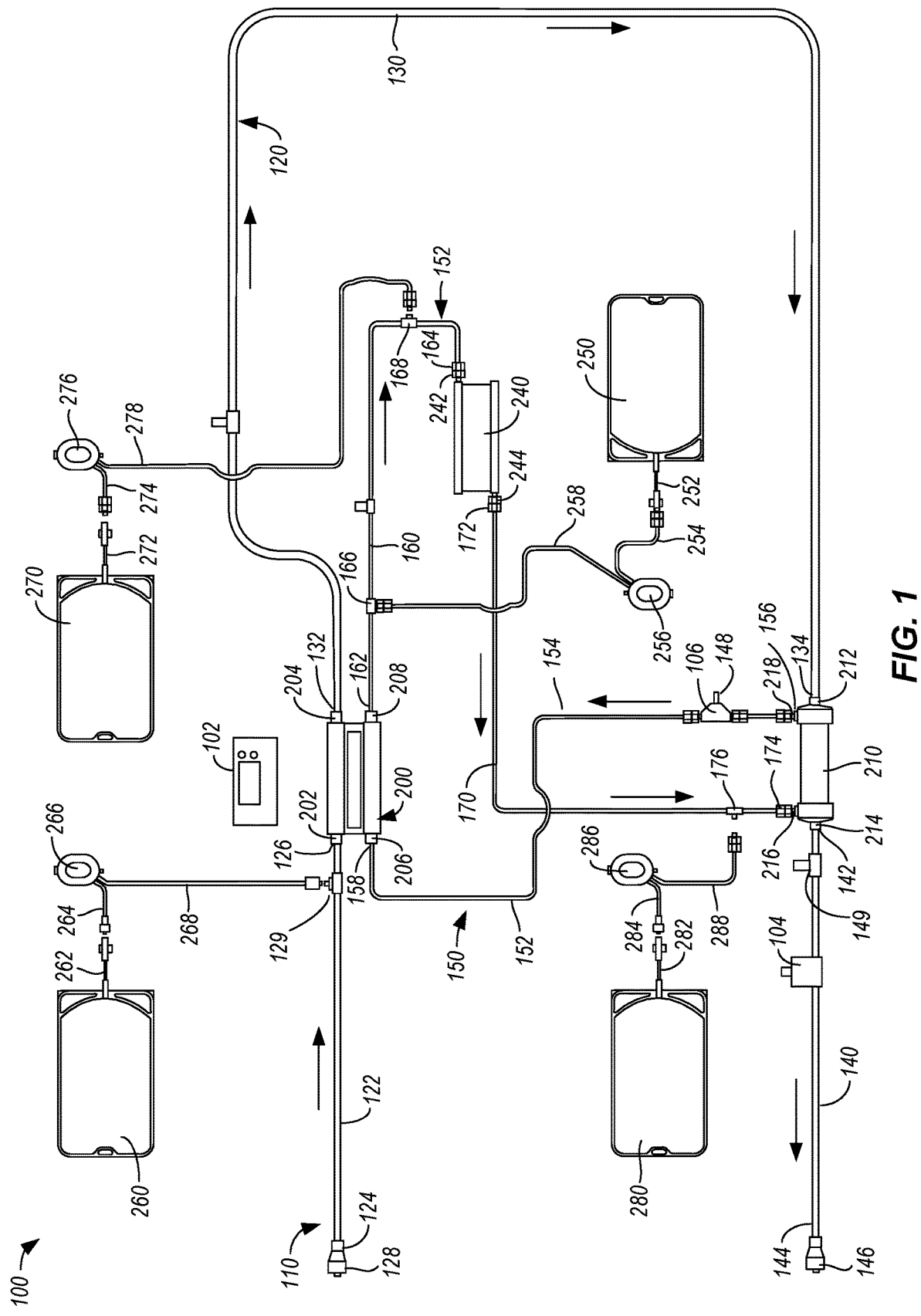
FIG. 1 is a schematic diagram of an example of a wearable daytime dialysis system.

While some embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Hemodialysis, also spelled haemodialysis, commonly called kidney dialysis or simply dialysis, is a process of purifying the blood of a person whose kidneys are not working normally. This type of dialysis achieves the extracorporeal removal of waste products such as creatinine and urea and free water from the blood when the kidneys are in a state of kidney failure. Hemodialysis can be an outpatient or inpatient therapy. Routine hemodialysis is conducted in a dialysis outpatient facility, either in a purpose built room in a hospital or a dedicated, stand-alone clinic. Less frequently hemodialysis is done at home. Dialysis treatments in a clinic are initiated and managed by specialized staff made up of nurses and technicians; dialysis treatments at home can be self-initiated and managed or done jointly with the assistance of a trained helper.

Conventional hemodialysis however has a number of disadvantages including: restricted independence, as people undergoing this procedure cannot travel around because of supplies' availability and being tethered to a large stationary device during treatment; requires high water quality; a large quantity of water; and continuous source of electricity, typically provided by a power plug connected to an outlet; requires reliable technology like dialysis machines; requires care givers having more knowledge of the complicated procedure and equipment; requires ongoing and repetitive time to set up and clean dialysis machines.

Additionally, hemodialysis often involves fluid removal (through ultrafiltration), because most patients with renal failure pass little or no urine. Side effects caused by removing too much fluid and/or removing fluid too rapidly include low blood pressure, fatigue, chest pains, leg-cramps, nausea and headaches. These symptoms can occur during the treatment and can persist post treatment; they are sometimes collectively referred to as the dialysis hangover or dialysis washout. The severity of these symptoms is usually proportionate to the amount and speed of fluid removal. However, the impact of a given amount or rate of fluid removal can vary greatly from person to person and day to day.

There are three types of hemodialysis: conventional hemodialysis, daily hemodialysis, and nocturnal hemodialysis. Conventional hemodialysis is usually done three times per week, for about 3-4 hours for each treatment, during which the patient's blood is drawn out through a tube at a rate of 200-400 mL/min. The tube is connected to a 15, 16, or 17 gauge needle inserted in the dialysis fistula or graft, or connected to one port of a dialysis catheter. The blood is then pumped through the dialyzer, and then the processed blood is pumped back into the patient's bloodstream through another tube (connected to a second needle or port). During the procedure, the patient's blood pressure is closely monitored, and if it becomes low, or the patient develops any other signs of low blood volume such as nausea, the dialysis attendant can administer extra fluid through the machine. During the treatment, the patient's entire blood volume (about 5000 cc) circulates through the machine every 15 minutes. During this process, the dialysis patient is exposed to a week's worth of water for the average person. Daily hemodialysis is typically used by those patients who do their own dialysis at home. It is less stressful (more gentle) but does require more frequent access. Daily hemodialysis is commonly done for 2 hours six days a week. The procedure of nocturnal hemodialysis is similar to conventional hemodialysis except it is typically performed three to six nights a week and between six and ten hours per session while the patient sleeps.

As used herein, and unless otherwise specified, the terms "first dialysis system", "untethered system" or "untethered" means or refers to the daytime dialysis system, capable of providing a user with the ability to move unconstrained.

As used herein, and unless otherwise specified, the term "second dialysis system", "tethered system" or "tethered" means or refers to the nighttime dialysis system, wherein the user's movement is restricted to that area immediately around the nighttime dialysis system.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range. In certain embodiments, the term "about" or "approximately" means within 1 hour, within 45 minutes, within 30 minutes, within 25 minutes, within 20 minutes, within 15 minutes, within 10 minutes, within 5 minutes, within 4 minutes, within 3 minutes within 2 minutes, or within 1 minute. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range.

As used herein, the terms "connected", "operationally connected", "coupled", "operationally coupled", "operationally linked", "operably connected", "operably coupled", "operably linked," and like terms, refer to a relationship (mechanical, linkage, coupling, etc.) between elements whereby operation of one element results in a corresponding, following, or simultaneous operation or actuation of a second element. It is noted that in using said terms to describe inventive embodiments, specific structures or mechanisms that link or couple the elements are typically described. However, unless otherwise specifically stated, when one of said terms is used, the term indicates that the actual linkage or coupling may take a variety of forms, which in certain instances will be readily apparent to a person of ordinary skill in the relevant technology.

As used herein, the terms "comprises", "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "user", "subject" or "patient" are used interchangeably. As used herein, the terms "subject" and "subjects" refers to an animal (e.g., birds, reptiles, and mammals), preferably a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old, 95 to 100 years old, or 100 to 120 years old.

Described herein are systems and methods related to a dialysis system which comprises both a component which performs dialysis functions during a period when the patient desires to be mobile, such as during the daytime, and a second component configured to perform dialysis functions during a period of time when mobility is not as important to the patient, such as during the nighttime. The patient can alternate use of the daytime dialysis system and the nighttime dialysis system, such as during a 24-hour period. The daytime dialysis system can be worn by the patients, such as under their clothes. The daytime dialysis system is lightweight and/or compact to facilitate transport of the system such that patients can maintain activities of daily life. Meanwhile, the nighttime dialysis system is configurable to provide additional toxin removal functions. The nighttime dialysis system is larger in size and/or heavier. The nighttime dialysis system is stationary, for example being configured to be positioned on a support. Use of the nighttime dialysis system enables use of the daytime dialysis system when the patient desires mobility. The combination of the daytime and nighttime dialysis systems enables a patient to be mobile during the day while maintaining overall desired removal of toxins.

It is important to note that certain toxins cannot be removed any faster than a steady rate over a 24 hour period. However, some toxins can be removed over shorter periods of time without negative consequences to the patient. Generally, there are two types of toxins: those bound to protein; and free toxins. Free toxins are generally considered to be more toxic. Examples of toxins that require removal over 24 hours include p-cresyl and indoxyl sulfate. These are part of a group of toxins called protein bound toxins (P-BUTS). The free form, which is the only toxic one, comes out in the urine, keeping its level low in a healthy patient. In dialysis the free fraction comes out on dialysis and the level of the free toxin is also low, however, as soon as the patient is on a dialysis machine, the protein bound toxins re-equilibrate with the free fraction, that comes up again to toxic levels. There are about 25 known P-BUTS. The combined system for hemodialysis comprising a first dialysis system and a second dialysis system configured to be used in combination, in an alternating fashion, keeps the P-BUTS low, at a non-toxic level. The charcoal sorbent, or other sorbents known in the art, continuously removes the free fraction of the P-BUTS over 24 hours. The other things that are best removed over 24 hours are sodium and water. Excessive removal of sodium and water over too short a period of time will result in hemodynamic problems. On the other hand, other substances known to be toxic, such as phosphorus and urea can be removed from the blood in sufficient amounts in 6-10 hours, thus not requiring longer periods for a sufficient removal. Urea and phosphorus are not P-BUTS. These can be removed using a builder nighttime dialysis system, The light-weight daytime dialysis system includes an activated carbon cartridge configured to adsorb various toxins from the dialysate. Optionally, in this embodiment or any embodiment disclosed herein, the daytime dialysis system does not include any other types of sorbent materials. For example, in some embodiments, the daytime dialysis system includes one activated carbon containing cartridge. The activated carbon is configured to remove one or more of creatinine and β2 micro globulins, p-cresol, indoleacetic acid, hippurate, and heavy metals, from the dialysate. The daytime dialysis system is not configured to remove urea from the blood flow.

The bulkier and heavier nighttime dialysis system is configured to remove urea. For example, in this embodiment or any embodiment disclosed herein, the nighttime dialysis system includes a urea converter to decompose urea removed from the blood stream into ammonia and carbon dioxide. The nighttime dialysis system is configured to remove the ammonia and vent the carbon dioxide to release the gas into the environment. The nighttime dialysis system can include a plurality of types of sorbent materials configured to regenerate the dialysate. For example, in some embodiments, the nighttime dialysis system includes a plurality of sorbent-containing cartridges to provide a plurality of types of sorbent materials. A patient can alternate use of the daytime dialysis system and a nighttime dialysis system, for example for about 12 hours each during a 24 hour period, such that the patient remains mobile during the day while maintaining overall desired removal of toxins.

FIG. 1 is a schematic diagram of one non-limiting example of a daytime dialysis system 100 according to some embodiments. The daytime dialysis system 100 is configurable to be transported by a patient, for example to perform toxin removal functions while a patient is mobile, such as during the daytime. The daytime dialysis system 100 is lightweight and/or compact in size to provide desired patient mobility. The daytime dialysis system 100 is configurable to be worn by the patient while the patient is going about his or her daily business without requiring tethering to external power sources or external components. For example, in some embodiments, the daytime dialysis system 100 is a wearable artificial kidney. As described in further details herein, the daytime dialysis system 100 is coupled to a belt such that the daytime dialysis system 100 is worn by the patient. It is to be understood that upon reading this disclosure, one of skill in the art will recognize that some components of the daytime system described herein are optional and need not be included in every configuration described herein.

In some embodiments, the daytime dialysis system 100 includes a control unit 102, a rechargeable battery 108, a blood circuit 110, an optional bubble detector 104 configured to detect presence of air bubbles in blood flowing through the blood circuit 110, a sterile dialysate circuit 150, and a blood detector 106 configured to detect presence of blood in the dialysate flowing in the dialysate circuit 150. In some embodiments, the blood circuit 110 is configured to flow blood through the daytime dialysis system 100, while the dialysate circuit 150 is configured to flow dialysate through the daytime dialysis system 100, preferably in counterflow directions, such that desired toxins are removed from the blood flow and into the dialysate, and the used dialysate is cleaned to provide regenerated dialysate. A pump 200 is included to drive blood flow and dialysate flow through the system 100. The blood circuit 110 is configured to flow blood received from the patient through the pump 200 and a dialyzer 210, where toxins are removed from the blood, before the blood is supplied back to the patient. The dialysate circuit 150 includes flow of the dialysate through the dialyzer 210, the pump 200, and the sorbent-containing cartridge 240. Toxins from the blood diffuse into the dialysate in the dialyzer 210, generating spent dialysate. The spent dialysate is subsequently regenerated using the sorbent-containing cartridge 240.

In some embodiments, the daytime dialysis system 100 includes an ultrafiltrate collector 250 configured to receive ultrafiltrate removed from the dialysate, as well as a sorbent-containing cartridge 240 configured to remove other toxins from the dialysate. The daytime dialysis system 100 also includes a blood thinner reservoir 260 configured to supply blood thinner into the blood circuit 110, such as heparin. The blood thinner reservoir 260 includes a reservoir inlet port 262 configured to be coupled a first channel 264. The first channel 264 is configured to provide fluid communication between the blood thinner pump 266 and the blood thinner reservoir 260. A second channel 268 is coupled to the blood thinner pump 266 to provide fluid communication between the blood thinner pump 266 and the blood circuit 110. The blood thinner pump 266 is used to control flow of blood thinner from the blood thinner reservoir 260 to the blood circuit 110. In any one of the embodiments, the blood thinner pump 266 is a micro-pump. In some embodiments, the daytime dialysis system 100 includes one or more optional electrolyte reservoirs to supplement the dialysate flow with electrolytes. As shown in FIG. 1, in some embodiments, the daytime dialysis system 100 optionally includes a first electrolyte reservoir 270 and an optional second electrolyte reservoir 280, such as one or more of sodium bicarbonate, magnesium and calcium.

In some embodiments, the first electrolyte reservoir 270 comprising sodium bicarbonate is optional, or unnecessary, when the daytime dialysis system 100 is primed with a primer solution containing bicarbonate ($HCO_3$). For example, when the dialysate circuit is initially primed with a primer solution, typically containing saline (or half-normal saline) and bicarbonate ($HCO_3$), the need for a separate electrolyte reservoir can be obviated.

As used herein, half-normal saline means saline (0.45% NaCl), often with "D5" (5% dextrose), contains 77 mEq/L of $Na^+$ and $Cl^-$ and 50 g/L dextrose. Alternative saline solutions may comprise: Hypertonic saline (7% NaCl solutions) may be used in perioperative fluid management protocols to reduce excessive intravenous fluid infusions and lessen pulmonary complications; and Quarter-normal saline (0.22% NaCl) has 39 mEq/L of $Na^+$ and $Cl^-$.

It is further noted that the systems described herein comprise a sterile dialysate circuit. Whereas one of skill in the art would recognize that the dialysate circuit of all dialysis machines in standard dialysis outpatient facilities are not, since they are one-pass systems. The dialysate used in the systems described herein, pass through the sorbent-containing cartridge(s) after the toxins are removed from the blood flow, and the used dialysate is cleaned during each pass through the system, allowing for a continuously circulating dialysate system. It also noted that as a precaution, the dialysate would/could be completely exchanged, and the system re-primed during each changeover between the daytime dialysis system and the nighttime dialysis system. Hence, the dialysate circulating through any one of the embodiments described herein would remain routinely sterile, thus avoiding any possibility of introducing infection.

The control unit 102 is in electrical communication with one or more components of the daytime dialysis system 100. For example, in some embodiments, the control unit 102 is in communication with the bubble detector 104 and the blood detector 106 such that an alarm is initiated when air bubbles are detected in the blood flow and/or blood is detected in the dialysate flow. In some embodiments, the control unit 102 is configured to pause and/or power down the system 100 upon detection of air bubbles in the blood flow and/or blood in the dialysate flow. In some embodiments, the control unit 102 is configured to control the pump 200 to provide desired flow of blood and/or dialysate through the system 100. The control unit 102 controls one or more optional pumps configured to control flow of electrolyte into the dialysate, blood thinner into the blood flow, and/or ultrafiltrate from the dialysate.

Referring again to FIG. 1, the pump 200 includes a blood inlet 202, a blood outlet 204, a dialysate inlet 206 and a dialysate outlet 208. Blood flow is driven through the pump 200 in a first direction while dialysate is driven through the pump in an opposing direction. In some embodiments, the pump 200 is a simultaneously.

The dialyzer 210 includes a blood inlet 212, a blood outlet 214, a dialysate inlet 216 and a dialysate outlet 218. Dialysate flow flows through the dialyzer 210 in a first direction while the blood flows through the dialyzer 210 in a counter current flow. Toxins from the blood flow diffuse into the dialysate across semi-porous membranes of the dialyzer 210 as the blood and dialysate flow across opposing surfaces of the semi-porous membranes. In a non-limiting example, blood flow can travel in a clockwise fashion through the blood circuit 110, while the dialysate can flow in a counterclockwise fashion through the dialysate circuit 150.

As shown in the non-limiting example of a daytime circuit as illustrated in FIG. 1, the blood circuit 110 includes blood flow tubing 120. The blood flow tubing 120 includes a first portion 122, a second portion 130 and a third portion 140. The first portion 120 is configured to deliver blood received from the patient to the pump 200. The first portion 122 includes a first end 124 and a second end 126. The first portion 122 includes a blood flow inlet 128 at the first end configured to receive blood from the patient, and the second end 126 is configured to be coupled to the pump 200. In some embodiments, the first portion 124 comprises a blood thinner infusion inlet 129 configured to be coupled to the blood thinner source 260, such that blood thinner from the blood thinner source 260 is able to be infused into the blood flow. Blood thinner is added into the blood flow to prevent blood clots from forming within the daytime dialysis system 100. In some embodiments, the blood thinner is heparin. In some embodiments, the blood thinner is a heparin alternative. In some embodiments, a heparin alternative includes: low molecular weight heparins, direct thrombin inhibitors, danaparoid, ancrod, r-hirudin, abeiximab, tirofiban and argatroban, among others known to those skilled in the art.

In some embodiments, the blood thinner infusion inlet 129 is positioned elsewhere on the blood circuit 120. For example, in some embodiments, the blood thinner infusion inlet 129 is positioned after pump 200, such as on the second portion 130 of the blood flow tubing 120.

The blood circuit 110 includes flow of blood from the first portion 122 of the blood flow tubing 120 through the pump 200 to the second portion 130 of the blood flow tubing 120. The second portion 130 is configured to deliver blood from the pump 200 to the dialyzer 210. The second portion 130 includes a first end 132 configured for coupling to the pump 200 and a second end 134 configured for coupling to the dialyzer 210. The first end 132 is coupled to the blood outlet port 204 of the pump 200 and the second end 134 is coupled to the blood inlet port 212 of the dialyzer 210. The blood flows through the dialyzer 210 to the third portion 140 of the blood tubing 120. The third portion 140 of the blood tubing 120 includes a first end 142 coupled to the dialyzer 210, such as the blood outlet port 214 of the dialyzer 210, and a blood flow outlet 146 at a second end 144 to permit flow therethrough of blood exiting from the dialyzer 210.

In some embodiments of a system for hemodialysis described herein, the system further comprises an optional pH sensor 149, tied to the control unit 102 to test for ammonia in the blood circuit. Ideally, the optional pH sensor 149 would be positioned between the dialyzer 210 and the second end 144.

Since ammonia is such a strong base, the optional pH sensor 149 provides a safety mechanism to detect when the sorbent-containing cartridges are no longer effective for removing ammonia from the system. The optional pH sensor 149 is in fluid communication with the blood flow exiting the dialyzer 210 such that the presence of ammonia within the fluid is detected and communicated to the control unit 102. The control unit 102 is configurable to pause and/or power off the system 100 upon detection of ammonia within the blood flow.

In some embodiments, the third portion 140 includes a bubble detector access port 148 configured for coupling to the bubble detector 104. The bubble detector 104 is in fluid communication with the blood flow exiting the dialyzer 210 such that presence of air bubbles within the flood is detected and communicated to the control unit 102. The control unit 102 is configurable to pause and/or power off the system 100 upon detection of air bubbles within the blood flow.

As shown in the non-limiting example of a daytime circuit as illustrated in FIG. 1, the sterile dialysate circuit 150 comprises a dialysate flow tubing 152. The dialysate flow tubing 152 includes a first portion 154 extending between the dialyzer 210 and the pump 200, a second portion 160 extending between the pump 200 and the sorbent-containing cartridge 240, and a third portion 170 between the sorbent-containing cartridge 240 and the dialyzer 210. The first portion 154 has a first end 156 and a second end 158. The first end 156 is coupled to the dialysate outlet port 218 of the dialyzer 210 and the second end 158 is coupled to the dialysate inlet port 206 of the pump 200. The first portion 154 of the dialysate circuit 150 comprises a blood detection access port. The blood detection access port is configured to couple the blood detector 106, such that presence of blood in the dialysate exiting the dialyzer 210 can be detected. In some embodiments, breakage in the membranes of the dialyzer 210 results in blood entering the dialysate flow. The blood detector 106 is in communication with the control unit 102 such that the control unit 102 will pause and/or power off the system 100 upon detection of blood in the dialysate.

Dialysate is driven by the pump 200 from the first dialysate tubing portion 154 to the second dialysate tubing portion 160. Referring again to FIG. 1, the second portion 160 of the dialysate circuit 150 has a first end 162 coupled to the dialysate outlet port 208 of the pump 200 and a second end 164 coupled to a dialysate inlet port 242 of the sorbent-containing cartridge 240. In some embodiments, the second portion 160 includes an ultrafiltrate outlet port 166 configured to couple to an ultrafiltrate collector 250. For example, ultrafiltrate from the dialysate exits the dialysate circuit 150 through the ultrafiltrate outlet port 166 in the second portion 160 of the dialysate tubing 152 and the ultrafiltrate is collected within the ultrafiltrate collector 250. The ultrafiltrate collector 250 includes an ultrafiltrate inlet port 252 configured to be coupled a first channel 254. The first channel 254 is configured to provide fluid communication between the ultrafiltrate pump 256 and the ultrafiltrate collector 250. A second channel 258 is coupled to the ultrafiltrate pump 256 to provide fluid communication between the ultrafiltrate pump 256 and the dialysate circuit 150. The ultrafiltrate pump 256 is used to control flow of ultrafiltrate from the dialysate circuit 150 into the ultrafiltrate collector 250. In any one of the embodiments, the ultrafiltrate pump 256 is a micro-pump. Removal of ultrafiltrate can provide removal of water and sodium from the dialysate. For example, the ultrafiltrate removal rate can be maintained at a physiological rate in order to reduce or avoid blunt hemodynamic changes.

In some embodiments, the dialysate flows through the second portion 160 of the dialysate tubing 152 into the sorbent-containing cartridge 240 via a dialysate inlet port 242. The dialysate flows through the sorbent-containing cartridge 240, exit via the dialysate outlet port 244, and through the third portion 170 of the dialysate tubing 152 to the dialyzer 210. The third portion 170 of the dialysate circuit 150 includes a first end 172 configured to be coupled to the dialysate outlet port 244 of the sorbent-containing cartridge 240, and a second end 174 configured to be coupled to the dialysate inlet port 216 of the dialyzer 210.

In some embodiments, the sorbent-containing cartridge 240 is configured to remove one or more of organic uremic metabolites and heavy metals. In some embodiments, the sorbent-containing cartridge 240 is configured to remove one or more of creatinine, uric acid and (32 micro globulins, p-cresol, indoleacetic acid and hippurate. The sorbent-containing cartridge 240 comprises activated carbon, such as charcoal. The dialysate exiting the sorbent-containing cartridge 240 is regenerated dialysate, such that dialysate entering the dialyzer 210 is cleaned dialysate.

In some embodiments, the dialysate circuit 150 of the daytime dialysis system 100 optionally includes one or more points at which optional electrolyte is infusible into the dialysate flow. One or more types of optional electrolyte solutions can be added into the dialysate flow to facilitate maintaining electrolyte homeostasis. For example, in some embodiments, one or more of optional electrolyte supplement solutions, such as electrolyte supplement solutions comprising sodium bicarbonate, calcium, and/or magnesium, can be infused into the dialysate flow at one or more optional electrolyte infusion points.

In some embodiments, the second portion 160 of the dialysate circuit 150 optionally includes a first optional electrolyte infusion port 168. The first optional electrolyte infusion port 168 is between the ultrafiltrate outlet port 166 and the second end 164 of the second portion 160. The first optional electrolyte infusion port 168 is configurable to be coupled to a first optional electrolyte reservoir 270. The first optional electrolyte reservoir 270 is configured to retain a first optional electrolyte solution. In some embodiments, the first optional electrolyte solution is used to adjust the pH of the dialysate. In some embodiments, the first optional electrolyte solution is a sodium bicarbonate solution. The first optional electrolyte solution is infused into the dialysate flow via the first optional electrolyte infusion port 168. Flow of the first optional electrolyte solution into the dialysate flow is controlled by a first optional electrolyte solution pump 276. The first optional electrolyte reservoir 270 comprises a first optional electrolyte outlet port 272 configured to be coupled to a first channel 274 extending between the outlet port 272 and the first optional electrolyte solution pump 276. A second channel 278 extends between the first optional electrolyte solution pump 276 and the dialysate circuit 150, for example coupling to the first optional electrolyte solution pump 276 on one end and to the first optional electrolyte infusion port 168 on a second end. In any one of the embodiments, the first optional electrolyte solution pump 276 is a micro-pump. In some embodiments, the first optional electrolyte solution pump 276 is configured to pump up to about 5 milliliters per hour (mL/hr), or for example from about 1 mL/hr to about 2 mL/hr, up to about 5 mL/hr.

In some embodiments, the third portion 170 of the dialysate circuit 150 includes a second optional electrolyte infusion port 176. The second optional electrolyte infusion port 176 is configured to be coupled to a second optional electrolyte reservoir 280. The second optional electrolyte reservoir 280 is configured to retain a second electrolyte solution. In some embodiments, the second optional electrolyte solution is a solution comprising calcium and magnesium. The second optional electrolyte solution is infused into the dialysate flow via the second optional electrolyte infusion port 176. Flow of the second optional electrolyte solution into the dialysate flow is controlled by a second electrolyte solution pump 286. The second optional electrolyte reservoir 280 comprises a second optional electrolyte outlet port 282 configured to be coupled to a first channel 284 extending between the outlet port 282 and the second optional electrolyte solution pump 286. A second channel 288 extends between the second optional electrolyte solution pump 286 and the dialysate circuit 150, for example coupling to the second optional electrolyte solution pump 286 on one end and to the electrolyte infusion port 176 on a second end. In any one of the embodiments, the second optional electrolyte solution pump 286 can be a micro-pump. In some embodiments, the second optional electrolyte solution pump 286 can be configured to pump up to about 5 milliliters per hour (mL/hr), or for example from about 1 mL/hr to about 2 mL/hr, up to about 5 mL/hr. In some embodiments, the daytime dialysis system 100 does not include the second optional electrolyte reservoir 280. For example, an electrolyte solution comprising calcium and magnesium is not added into the dialysate flow.

Figure 2:
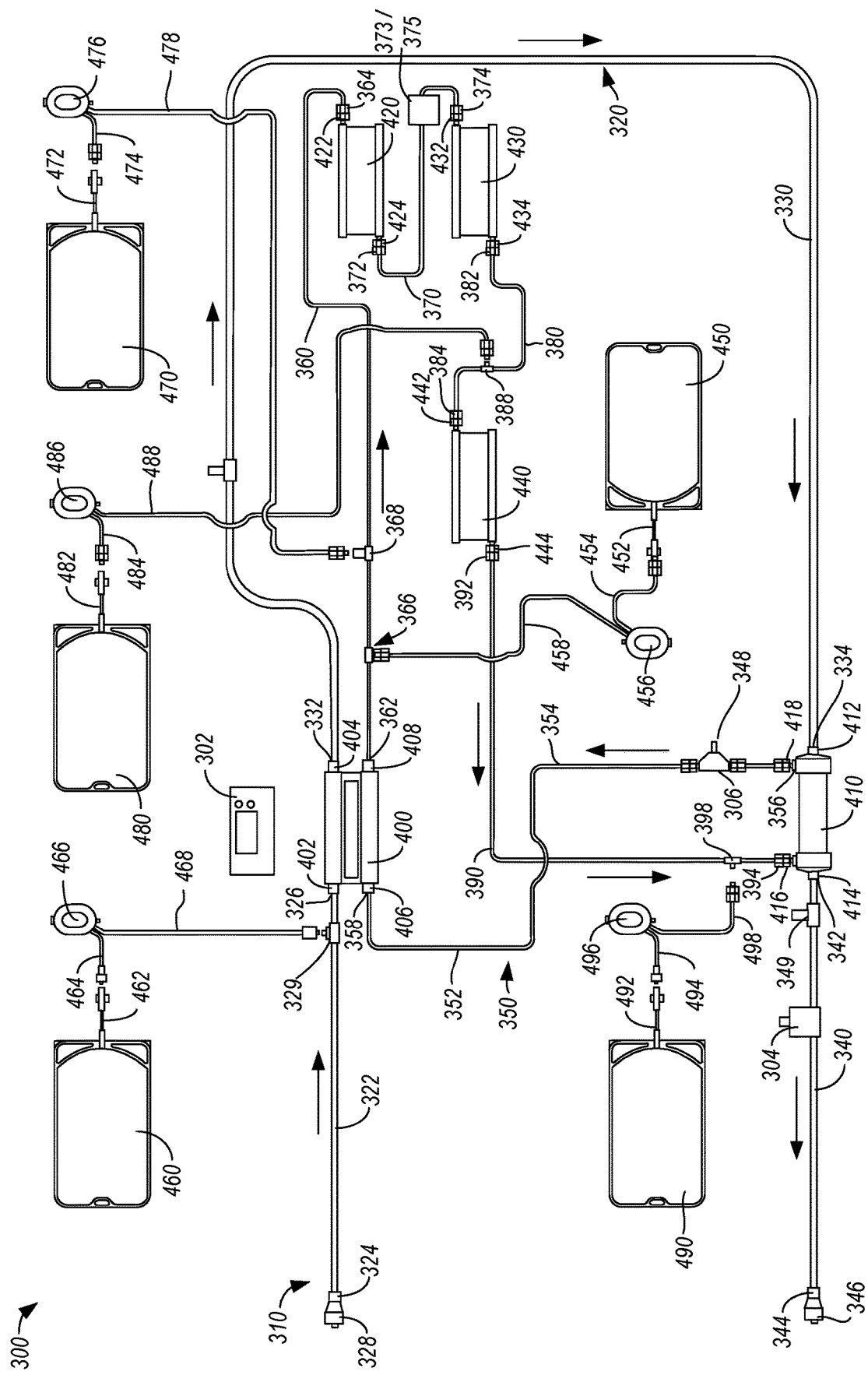
FIG. 2 is a schematic diagram of an example of a nighttime dialysis system.

FIG. 2 is a schematic diagram of an example of a nighttime dialysis system 300 according to some embodiments. The nighttime dialysis system 300 is configured not to be worn by the patient. The nighttime dialysis system 300 is configured to be positioned on a support independent of the patient. In some embodiments, the nighttime dialysis system 300 is configured to be a stationary, for example being configured to be placed on a stationary support next to the bed of the patient. In some embodiments, the stationary support includes a bedside table. In some embodiments, the nighttime dialysis system 300 is hung, such as from a pole placed next to the bed. In some embodiments, the nighttime dialysis system 300 is configurable for placement in the bed of a patient, such as in a protective or padded covering. The nighttime dialysis system 300 is configured to include additional toxin removal functions, such as removal of urea, as compared to a daytime dialysis system (e.g., the daytime dialysis system 100 of FIG. 1). As the nighttime dialysis system 300 is typically positioned on a support, instead of being worn by a patient, the nighttime dialysis system 300 is generally configured to be heavier in weight and/or larger in size. The nighttime dialysis system 300 is configured to perform the additional toxin removal functions while the patient is able to have the dialysis system 300 on a support, such that the patient can use the lighter and/or smaller daytime dialysis system while the patient is typically mobile. For example, alternating use between the nighttime dialysis system 300 and the daytime dialysis system provides the patient desired water and sodium removal and nitrogen balance, such as during a 24-hour period. In some embodiments, the daytime dialysis system is used for about 8 to about 16 continuous hours, and the nighttime dialysis system 300 is used for about 8 to about 16 continuous hours. For example, the daytime dialysis system 100 is used for about 12 continuous hours, and the nighttime dialysis system 300 is used for about 12 continuous hours. In some embodiments, the daytime dialysis system 100 is used for about 8 continuous hours, about 10 continuous hours, about 12 continuous hours, about 14 continuous hours, or about 16 continuous hours. In some embodiments, the nighttime dialysis system 300 is used, for about 8 continuous hours, about 10 continuous hours, about 12 continuous hours, about 14 continuous hours, or about 16 continuous hours.

In some embodiments, the nighttime dialysis system 300 includes a control unit 302, a battery 308, a blood circuit 310, a bubble detector 304 configured to detect presence of air bubbles in blood flowing through the blood circuit 310, a sterile dialysate circuit 350, and a blood detector 306 configured to detect presence of blood in the dialysate flowing in the dialysate circuit 350. A side-to-side pulsatile pump 400 is included to drive blood flow and dialysate flow. The sterile dialysate circuit 350 includes flow of the dialysate through the dialyzer 410, the side-to-side pulsatile pump 400, and a plurality of cartridges. In some embodiments, the dialysate circuit 350 includes an ultrafiltrate collector 450 configured to receive ultrafiltrate removed from the dialysate. The dialysate circuit 350 includes a urea converter 420 configured to remove urea from the dialysate, as well as a first sorbent-containing cartridge 430 and a second sorbent-containing cartridge 440.

In some embodiments, the nighttime dialysis system 300 also includes an optional blood thinner reservoir 460 configured to supply blood thinner, such as heparin, into the blood circuit 310. The blood thinner reservoir 460 includes a reservoir inlet port 462 configured to be coupled a first channel 464. The first channel 464 is configured to provide fluid communication between the blood thinner pump 466 and the blood thinner reservoir 460. A second channel 468 is coupled to the blood thinner pump 466 to provide fluid communication between the blood thinner pump 466 and the blood circuit 310. The blood thinner pump 466 is used to control flow of blood thinner from the blood thinner reservoir 460 to the blood circuit 410. In any one of the embodiments, the blood thinner pump 466 is a micro-pump. In some embodiments, the nighttime dialysis system 300 includes one or more optional electrolyte reservoirs to supplement the dialysate flow with optional electrolytes, including for example an optional first electrolyte reservoir 470, a second optional electrolyte reservoir 480 and a third optional electrolyte reservoir 490.

The control unit 302 is in electrical communication with one or more components of the nighttime dialysis system 300. For example, in some embodiments, the control unit 302 is in communication with the optional bubble detector 304 and the blood detector 306 such that an alarm is initiated when air bubbles are detected in the blood flow and/or blood is detected in the dialysate flow. In some embodiments, the control unit 302 is configured to pause and/or power down the system 300 upon detection of air bubbles in the blood flow and/or blood in the dialysate flow. In some embodiments, the control unit 302 is configured to control the side-to-side pulsatile pump 400 to provide desired flow of blood and/or dialysate through the system 300. In some embodiments, the control unit 302 controls one or more optional pumps configured to control flow of optional electrolyte into the dialysate, blood thinner into the blood flow, and/or ultrafiltrate from the dialysate.

The blood circuit 310 is configured to receive blood from the patient and flow the blood through a side-to-side pulsatile pump 400 and a dialyzer 410, before the blood is supplied back to the patient. In some embodiments, the sterile dialysate circuit 350 is configured to flow dialysate through the dialyzer 410, the side-to-side pulsatile pump 400, and a urea converter cartridge 420, a first cartridge 430 and a second sorbent-containing cartridge 440.

In some embodiments, the side-to-side pulsatile pump 400 includes a blood inlet 402, a blood outlet 404, a dialysate inlet 406 and a dialysate outlet 408. Blood flow is driven through the pump 400 in a first direction while dialysate is driven through the side-to-side pulsatile pump 400 in an opposing direction. In some embodiments, the side-to-side pulsatile pump 400 is a dual channel pump. The dialyzer 410 includes a blood inlet 412, a blood outlet 414, a dialysate inlet 416 and a dialysate outlet 418. In some embodiments, dialysate flows through the dialyzer 410 in a first direction while blood flows through the dialyzer 410 in a second opposing direction. In a non-limiting example, blood flow can travel in a clockwise fashion through the blood circuit 310, while the dialysate can travel in a counterclockwise fashion through the sterile dialysate circuit 350.

The blood circuit 310 includes blood flow tubing 320. In some embodiments, the blood flow tubing 320 includes a first portion 322, a second portion 330 and a third portion 340. The first portion 322 is configured to deliver blood received from the patient to a pump such as the side-to-side pulsatile pump 400 described in more detail below. The first portion 322 includes a first end 324 and a second end 326. The first portion 322 includes a blood flow inlet 328 at the first end configured to receive blood from the patient, and the second end 326 is configured to be coupled to the side-to-side pulsatile pump 400. In some embodiments, the first portion 322 comprises a blood thinner infusion inlet 329 configured to be coupled to the blood thinner source 460, such that blood thinner from the blood thinner source 460 can be infused into the blood flow. Blood thinner is added into the blood flow to prevent blood clots from forming within the nighttime dialysis system 300. In some embodiments, the blood thinner is heparin. In some embodiments, the blood thinner is a heparin alternative. In some embodiments, a heparin alternative includes: low molecular weight heparins, direct thrombin inhibitors, danaparoid, ancrod, r-hirudin, abeiximab, tirofiban and argatroban, among others known to those skilled in the art. In some embodiments, the blood thinner infusion inlet 329 is positioned elsewhere on the blood circuit 310. For example, the blood thinner infusion inlet 329 is positioned after side-to-side pulsatile pump 400, such as on the second portion 330 of the blood flow tubing 320.

As shown in FIG. 2, the blood circuit 310 includes a flow of blood from the first portion 322 of the blood flow tubing 320 through the side-to-side pulsatile pump 400 to the second portion 330 of the blood flow tubing 320. In some embodiments, the second portion 330 is configured to deliver blood from the side-to-side pulsatile pump 400 to the dialyzer 410. The second portion 330 includes a first end 332 configured for coupling to the side-to-side pulsatile pump 400 and a second end 334 configured for coupling to the dialyzer 410. The first end 332 is coupled to the blood outlet 404 of the side-to-side pulsatile pump 400 and the second end 334 is coupled to the blood inlet 412 of the dialyzer 410. The blood flows through the dialyzer 410 to the third portion 340 of the blood tubing 320. The third portion 340 of the blood tubing 320 includes a first end 342 and a second end 344. The first end 342 is configured to be coupled to the dialyzer 410, such as at the blood outlet 414 of the dialyzer 410. A blood flow outlet 346 is at the second end 344 to permit flow therethrough of blood exiting from the dialyzer 410. In some embodiments, the third portion 340 includes a blood detection access port 348 configured for coupling to the bubble detector 304.

Optionally, in any one of the embodiments of a system for hemodialysis described herein, the system further comprises an optional pH sensor 349, tied to the control unit 302 to test for ammonia in the blood circuit. Ideally, the optional pH sensor 349 would be positioned between the dialyzer 410 and the second end 344. The optional pH sensor 349 is in fluid communication with the blood flow exiting the dialyzer 410 such that the presence of ammonia within the fluid is detected and communicated to the control unit 302. The control unit 302 is configurable to pause and/or power off the system 300 upon detection of ammonia within the blood flow.

The sterile dialysate circuit 350 comprises a dialysate tubing 352 comprising a first portion 354 extending between the dialyzer 410 and the pump 400, a second portion 360 extending between the pump 400 and the urea converter cartridge 420, a third portion 370 between the urea converter cartridge 420 and the first sorbent-containing cartridge 430, a fourth portion 380 between the first sorbent-containing cartridge 430 and the second sorbent-containing cartridge 440, and a fifth portion 390 between the second sorbent-containing cartridge 440 and the dialyzer 410.

The first portion 354 has a first end 356 and a second end 358. In some embodiments, the first end 356 is coupled to the dialysate outlet 418 of the dialyzer 410 and the second end 358 is coupled to the dialysate inlet 406 of the side-to-side pulsatile pump 400. In some embodiments, the first portion 354 of the dialysate circuit 350 comprises a blood detection access port 348. The blood detection access port 348 is configured to couple a blood detector 306, such that presence of blood in the dialysate exiting the dialyzer 410 can be detected.

In some embodiments, the second portion 360 of the dialysate tubing 352 of the second portion 360 has a first end 362 coupled to the dialysate exit 408 of the side-to-side pulsatile pump 400 and a second end 364 coupled to a dialysate inlet 422 of the urea converter cartridge 420. In some embodiments, the second portion 360 includes an ultrafiltrate exit port 366 configured to couple to an ultrafiltrate collector 450. For example, ultrafiltrate exits the dialysate circuit 350 through the ultrafiltrate exit port 366 in the second portion 360 of the dialysate tubing 352, and is retained in the ultrafiltrate collector 450. Flow of the ultrafiltrate from the dialysate flow to the ultrafiltrate collector 450 is via a first ultrafiltrate channel 454 coupled to an exit port 452 of the ultrafiltrate collector 450 and an ultrafiltrate pump 456, and a second ultrafiltrate channel 458 coupled to the ultrafiltrate pump 456 and the second portion 360 of the dialysate tubing 352. Flow of the ultrafiltrate from the dialysate circuit 350 is controlled by the ultrafiltrate pump 456. In any one of the embodiments, the ultrafiltrate pump 456 is a micro-pump. Removal of ultrafiltrate can provide removal of water and sodium from the dialysate. The ultrafiltrate removal rate can be maintained at a physiological rate. As described herein, ultrafiltrate removal can also be provided in a daytime dialysis system. Maintaining continued removal of ultrafiltrate using both the daytime dialysis system and the nighttime dialysis system can reduce or avoid blunt hemodynamic changes.

The urea converter cartridge 420 is configured to convert urea to ammonium carbonate, which in the presence of hydrogen ions generates carbon dioxide. For example, in some embodiments, the urea converter cartridge comprises urease. In some embodiments, the urea converter cartridge 420 comprises one or more sorbent materials configured to adsorb toxins in the dialysate. The one or more sorbent materials are configurable to adsorb ammonium, such as the ammonium generated by the degradation of urea into ammonium carbonate. In some embodiments, the one or more sorbent materials are configurable to adsorb other cations, including cations of calcium, magnesium, and/or potassium. In some embodiments, the urea converter cartridge 420 comprises zirconium phosphate. For example, zirconium phosphate in the urea converter cartridge 420 can remove ammonium from the dialysate, along with calcium, magnesium and potassium cations, while releasing sodium and hydrogen ions.

Optionally in any embodiment, the nighttime dialysis system 300 includes a gas removal component. As described herein, gas such as carbon dioxide can be generated in the dialysate regeneration process. The nighttime dialysis system 300 includes a gas removal component to provide desired elimination of the gas, including for example a gas venting feature, such as a bubble trap, and/or a degasser. In any of the embodiments, the nighttime dialysis system 300 includes a gas removal component comprising, for example, a vacuum chamber that draws a vacuum and pulls bubbles out of the fluid. In some embodiments, the vacuum chamber is configured such that it maintains vertical position such that any gas present rises to the top of the system. In some embodiments, the nighttime dialysis system 300 is configurable such that the components can be placed in a pillow, stuffed animal or similar type of "camouflaging" covering. Such a camouflaging covering would be useful for systems utilized with children or persons requiring a "comfort" device. In some embodiments, the nighttime dialysis system 300 includes a weight configured to maintain an upright position of the system, in order for the gas removal component to properly function.

In some embodiments, the urea converter cartridge 420 comprises more than one distinct cartridge and/or distinct portions of cartridges. For example, in some embodiments, the urea converter cartridge 420 is configurable to be split into more than one distinct cartridge. The urea converter cartridge 420 comprises one or more cartridges to retain the urea converter component, such as the urease, and one or more cartridges to retain the one or more sorbent materials. For example, in some embodiments, the urea converter cartridge 420 comprises a first cartridge configured to retain the urease and a second cartridge configured to retain the one or more sorbent materials. In some embodiments, the urea converter cartridge 420 comprises more than one distinct portions, with one or more respective portions comprising the urease and one or more sorbent materials.

In some embodiments, the gas removal component 375 is in fluid communication with the dialysate circuit 350 between the urea converter cartridge 420 and the first sorbent-containing cartridge 430. For example, in some embodiments, the third portion 370 of the dialysate tubing 352 has a gas removal component access port 373 between a first end 372 coupled to the urea converter cartridge 420 and a second end 374 coupled to the first sorbent-containing cartridge 430. The gas removal component access port is positioned between the first end 372 and the second end 374, and is configured to be coupled to a gas removal component 375. In some embodiments, the gas removal component access port of the dialysis circuit 350 is configured to be coupled to a gas degasser. In some embodiments, the gas removal component access port can be configured to be coupled to a venting feature, including a bubble trap. For example, the gas removal component access port is configurable for venting gas into the surrounding atmosphere, such as through a semipermeable membrane. In some embodiments, the gas removal component access port 373 can be configured to be coupled to a vacuum chamber.

In some embodiments, the gas removal component 375 is in fluid communication with the dialysate circuit 350 between the distinct cartridges or distinct cartridge portions of a urea converter cartridge. For example, in some embodiments, the urea converter cartridge 420 comprises a first cartridge configured to retain the urease and a second cartridge configured to retain the one or more sorbent materials, and the gas removal component 375 is positionable between the first cartridge and the second cartridge.

Referring again to FIG. 2, in some embodiments, the dialysate circuit 350 includes the first sorbent-containing cartridge 430. The first sorbent-containing cartridge 430 is configurable to remove one or more heavy metals and/or one or more anions from the dialysate. For example, the first sorbent-containing cartridge 430 is configured to remove one or more of iron, mercury and aluminum. In some embodiments, first sorbent-containing cartridge 430 is configured to remove one or more phosphate and sulfide anions. In some embodiments, the first sorbent-containing cartridge 430 comprises hydrous zirconium oxide. For example, dialysate flows through the urea converter cartridge 420, exits the dialysate exit port 424 of the urea converter cartridge 420, through the third portion 370 of the dialysate tubing 352, and into the first sorbent-containing cartridge 430 via the dialysate inlet port 432 where heavy metals, such as iron, mercury and aluminum, and phosphate and sulfide anions are removed from the dialysate, in exchange for acetate. Zirconium hydroxide binds phosphate and releases acetate, bicarbonate and sodium in small amounts. Zirconium phosphate removes ammonium, calcium, magnesium and potassium.

In some embodiments, the dialysate exits the first sorbent-containing cartridge 430 through the first sorbent-containing cartridge exit port 434, and flows through the fourth portion 380 of the dialysate tubing 352. The fourth portion 380 comprises a first end 382 configured to be coupled to the exit port 434 of the first sorbent-containing cartridge 430 and a second end 384 configured to be coupled to a dialysate inlet port 442 of the second sorbent-containing cartridge 440.

The second sorbent-containing cartridge 440 is configurable to remove one or more of organic uremic metabolites and heavy metals. In some embodiments, the second sorbent-containing cartridge 440 is configured to remove one or more of creatinine, uric acid and β2 micro globulins, p-cresol, indoleacetic acid and hippurate. The second sorbent-containing cartridge 440 comprises activated carbon, such as charcoal. In some embodiments, the second sorbent-containing cartridge 440 has characteristics similar to or the same as the sorbent-containing cartridge 240 described with reference to FIG. 1.

The dialysate which exits the dialysate exit port 444 of the second sorbent-containing cartridge 440 flows into the fifth portion 390 of the dialysate tubing 352. The fifth portion 390 of the dialysate tubing 352 has a first end 392 coupled to the dialysate exit port 444 of the second sorbent-containing cartridge 440 and a second end 394 coupled to the dialysate inlet port 416 of the dialyzer 410. The dialysate exiting the dialysate exit port 444 of the second sorbent-containing cartridge 440 is regenerated dialysate, such that dialysate flowing into the dialyzer 410 is cleaned dialysate which can be used to remove toxins from the blood of the patient.

Since the dialysate system is sterile, ideally, the dialysate would be changed between each conversion from the daytime dialysis system 100, to the nighttime dialysis system 300, or between each conversion from the nighttime dialysis system 300, to the daytime dialysis system 100.

As shown in FIG. 2, the dialysate circuit 350 of the nighttime dialysis system 300 includes various points at which optional electrolyte can be infused into the dialysate flow. One or more types of optional electrolyte solutions can be added into the dialysate flow to facilitate maintaining electrolyte homeostasis. For example, one or more of electrolyte supplement solutions, such as optional electrolyte supplement solutions comprising sodium bicarbonate, calcium, and/or magnesium, can be infused into the dialysate flow at one or more optional electrolyte infusion points.

In some embodiments, a first optional electrolyte solution is added to the dialysate flow via a first optional electrolyte infusion port 368 between the pump 400 and the urea converter cartridge 420. For example, the second portion 360 of the dialysate circuit 350 includes a first optional electrolyte infusion port 368. In some embodiments, the first optional electrolyte infusion port 368 is between the ultrafiltrate exit port 366 and the second end 364 of the second portion 360. The first optional electrolyte infusion port 368 is configured to be coupled to a first optional electrolyte reservoir 470 configured to retain a first optional electrolyte solution. The first optional electrolyte solution can include a variety of electrolyte supplements. In some embodiments, the first optional electrolyte solution is a glucose solution. In some embodiments, the first optional electrolyte solution is a solution comprising amino acids. In some embodiments, the first optional electrolyte solution is a solution comprising potassium. In some embodiments, the first optional electrolyte solution is infused into the dialysate flow via the first optional electrolyte infusion port 368 in the second portion 360 of the dialysate circuit 350. Flow of the first electrolyte solution into the dialysate flow is controlled by a first optional electrolyte infusion pump 476. The first optional electrolyte solution exits the first optional electrolyte reservoir 470 through a first optional electrolyte exit port 472 coupled to a first channel 474 extending between the exit port 472 and the first optional electrolyte infusion pump 476. In some embodiments, a second channel 478 extends between the first electrolyte infusion pump 476 and the dialysate circuit 350, such as the first electrolyte infusion port 368. The first electrolyte infusion pump 476 controls flow of the first optional electrolyte solution into the dialysate. In any one of the embodiments, the first optional electrolyte infusion pump 476 is a micro-pump. In some embodiments, the first optional electrolyte infusion pump 476 is configured to pump up to about 5 milliliters per hour (mL/hr). For example, in some embodiments, the first optional electrolyte infusion pump 476 is configurable to pump about 1 mL/hr to about 2 mL/hr of the first optional electrolyte solution into the dialysate flow. In some embodiments, the first optional electrolyte solution can be added to the dialysate later in the dialysate flow, such as at a position on the fifth portion 390 of the dialysate tubing 352.

In some embodiments, a second optional electrolyte solution is added to the dialysate flow via a second optional electrolyte infusion port 388 between the first sorbent-containing cartridge 430 and the second sorbent-containing cartridge 440. For example, the fourth portion 380 of the dialysate circuit 350 includes a second optional electrolyte infusion port 388. The second optional electrolyte infusion port 388 is configurable to be coupled to a second optional electrolyte reservoir 480 configured to retain a second optional electrolyte solution. In some embodiments, the second optional electrolyte solution is a sodium bicarbonate solution. The second optional electrolyte solution is infusible into the dialysate flow via the second optional electrolyte infusion port 388. Flow of the second optional electrolyte solution into the dialysate flow is controlled by a second optional electrolyte solution pump 486. The second optional electrolyte reservoir 480 comprises a second optional electrolyte exit port 482 configured to be coupled to a first channel 484 providing fluid communication between the exit port 482 and the second optional electrolyte solution pump 486. A second channel 488 extends between the second optional electrolyte solution pump 486 and the dialysate circuit 350, for example coupling to the second optional electrolyte solution pump 486 on one end and to the second optional electrolyte infusion port 388 on a second end. Flow of the second optional electrolyte solution into the dialysate is controlled by the second optional electrolyte solution pump 486. In any one of the embodiments, the second optional electrolyte solution pump 486 is a micro-pump. In some embodiments, the second optional electrolyte solution pump 486 is configured to pump up to about 5 milliliters per hour (mL/hr). For example, in some embodiments, the second optional electrolyte solution pump 486 is configurable to pump about 5 mL/hr of a sodium bicarbonate containing solution into the dialysate flow. For example, in some embodiments, the second optional electrolyte solution pump 486 is configurable to pump about 1 mL/hr to about 2 mL/hr of the sodium bicarbonate containing solution into the dialysate flow.

In some embodiments, the optional addition of sodium bicarbonate into the dialysate flow occurs at a position other than between the first sorbent-containing cartridge 430 and the second sorbent-containing cartridge 440. In some embodiments, sodium bicarbonate is infused into the dialysate flow at a position after a gas removal component, such as the gas removal component configured to remove carbon dioxide produced in the dialysate regeneration process. In some embodiments, the sodium bicarbonate is added between the urea converter cartridge 420 and the first sorbent-containing cartridge 430. For example, in some embodiments, the sodium bicarbonate is added to the dialysate flow at a position along the third portion 370 of the dialysate tubing 352 after a gas removal component access port.

In some embodiments, a third optional electrolyte solution is added to the dialysate flow via a third optional electrolyte infusion port 398 between the second sorbent-containing cartridge 440 and the dialyzer 410. For example, in some embodiments, the fifth portion 390 of the dialysate tubing 352 includes a third optional electrolyte infusion port 388 configured to receive a third optional electrolyte solution from a third optional electrolyte reservoir 490. In some embodiments, the third optional electrolyte solution comprises calcium and/or magnesium. For example, the third optional electrolyte solution is a calcium and magnesium-containing solution. In some embodiments, the third optional electrolyte solution is infused into the dialysate flow via the third optional electrolyte infusion port 398, where flow of the third optional electrolyte solution is controlled by a third optional electrolyte infusion pump 496. The third optional electrolyte reservoir 490 comprises a third optional electrolyte exit port 492 configured to be coupled to a first channel 494 extending between the exit port 492 and the third optional electrolyte infusion pump 496. A second channel 498 extends between the third optional electrolyte infusion pump 496 and the dialysate circuit 350, for example coupling to the third optional electrolyte infusion pump 496 on one end and to the third optional electrolyte infusion port 398 on a second end. The third optional electrolyte infusion pump 496 controls flow of the third optional electrolyte solution into the dialysate. In any one of the embodiments, the third optional electrolyte infusion pump 496 is a micro-pump. In some embodiments, the third optional electrolyte infusion pump 496 is configurable to pump up to about 5 milliliters per hour (mL/hr). For example, the third optional electrolyte infusion pump 496 can be configured to pump about 5 mL/hr of a solution containing calcium and magnesium into the dialysate flow. In some embodiments, the third optional electrolyte infusion pump 496 is configurable to pump about 1 mL/hr to about 2 mL/hr of the solution containing calcium and magnesium into the dialysate flow.

As described herein, a dialysis system can include both a system which performs dialysis functions during a period when the patient desires to be mobile, such as during the daytime, and a second system configured to perform dialysis functions during a period of time when mobility is not as important to the patient, such as during the nighttime, and where additional functions are performed by the second system during the period of time when mobility is less important. In some embodiments, instead of switching out the entire first system and replacing the first system with the second system, one or more components for performing the additional functions of the second system are releasably coupled to the first system. For example, one or more components of a nighttime dialysis system, such as the as the nighttime dialysis system described with reference to FIG. 2, not included in a daytime dialysis system, are releasably coupled to a daytime dialysis system to provide the additional toxin removal functions of a nighttime dialysis system. In some embodiments, a urea converter cartridge and a sorbent-containing cartridge comprising hydrous zirconium oxide are releasably coupled to a sterile dialysate circuit of the daytime dialysis system to provide the added urea removal functions of a nighttime dialysis system, instead of swapping out the entire daytime dialysis system when switching to the nighttime dialysis system. The urea converter and sorbent-containing cartridge is releasably coupled to the daytime dialysis system between a dual channel, side-to-side pulsatile pump and a sorbent-containing cartridge comprising activated carbon, such that the additional function of urea removal is provided. In some embodiments, one or more additional optional electrolyte reservoirs are added to a daytime dialysis system to convert the daytime dialysis system to a system which provides the functions of a nighttime dialysis system. The additional optional electrolyte reservoirs are releasably coupled to the dialysate circuit at positions as described with reference to FIG. 2.

In some embodiments, when components of the second dialysis system are attached to the first dialysis system, the second dialysis system comprises a power cord for attachment to an external power source and is configured to recharge the rechargeable battery of the first dialysis system so that when the second dialysis system is later disconnected and the patient is again able to freely move about untethered, the battery will again be fully charged and capable of powering the first dialysis system for a full period of continuous, untethered use.

Figure 3:
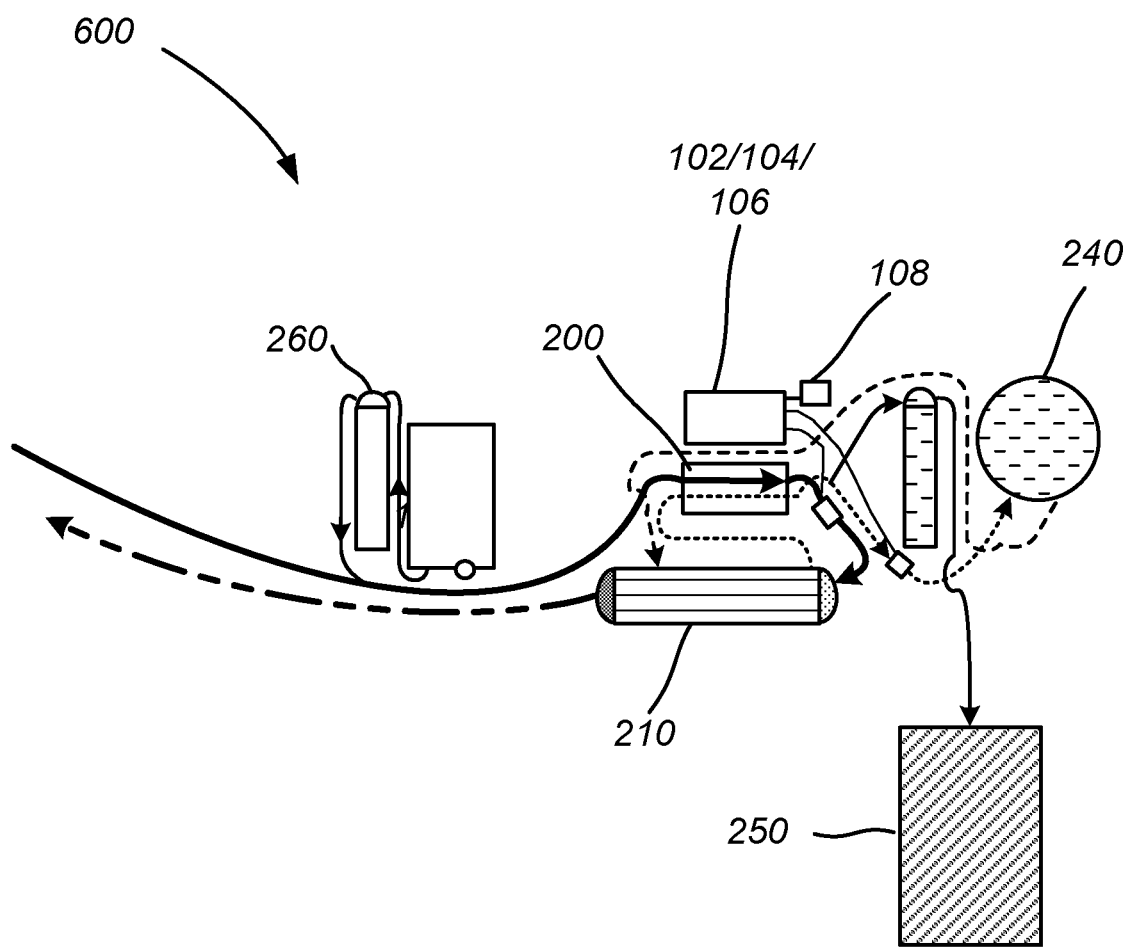
FIG. 3 is a schematic diagram of an example of a daytime dialysis system in a configuration configured to be coupled to a garment worn by a patient.

FIG. 3 is a schematic diagram of one non-limiting example of a daytime dialysis system 600 configured to be coupled to a wearable garment, such as a belt, such that the daytime dialysis system can be worn by a patient. The daytime dialysis system 600 can have one or more characteristics of the daytime dialysis system 100 as described with reference to FIG. 1. As shown in FIG. 3, the daytime dialysis system 600 can have its components, such as one or more dialysate regenerating components (e.g. 240), an optional blood thinner reservoir (260), one or more pumps (e.g. 200, 256, 266, 276), some pumps being optional, a dialyzer (e.g. 210), an optional electrolyte reservoir (not shown), blood detector (e.g. 106), an optional bubble detector (e.g. 104), rechargeable battery (e.g. 108), control unit (e.g. 102), and an ultrafiltrate collector (e.g. 250) arranged in a compact manner to facilitate transport of the daytime dialysis system 600 on a wearable garment, such as a belt for fastening around a patient's waist. As described herein, in some embodiments, the daytime dialysis system 600 can be configured such that the patient can transport the daytime dialysis system 600 under his or her clothing while the system is functioning to remove toxins from the patient's blood. It is to be understood that upon reading this disclosure, one of skill in the art will recognize that some components of the daytime system are optional and need not be included in every configuration described herein.

Figure 4:
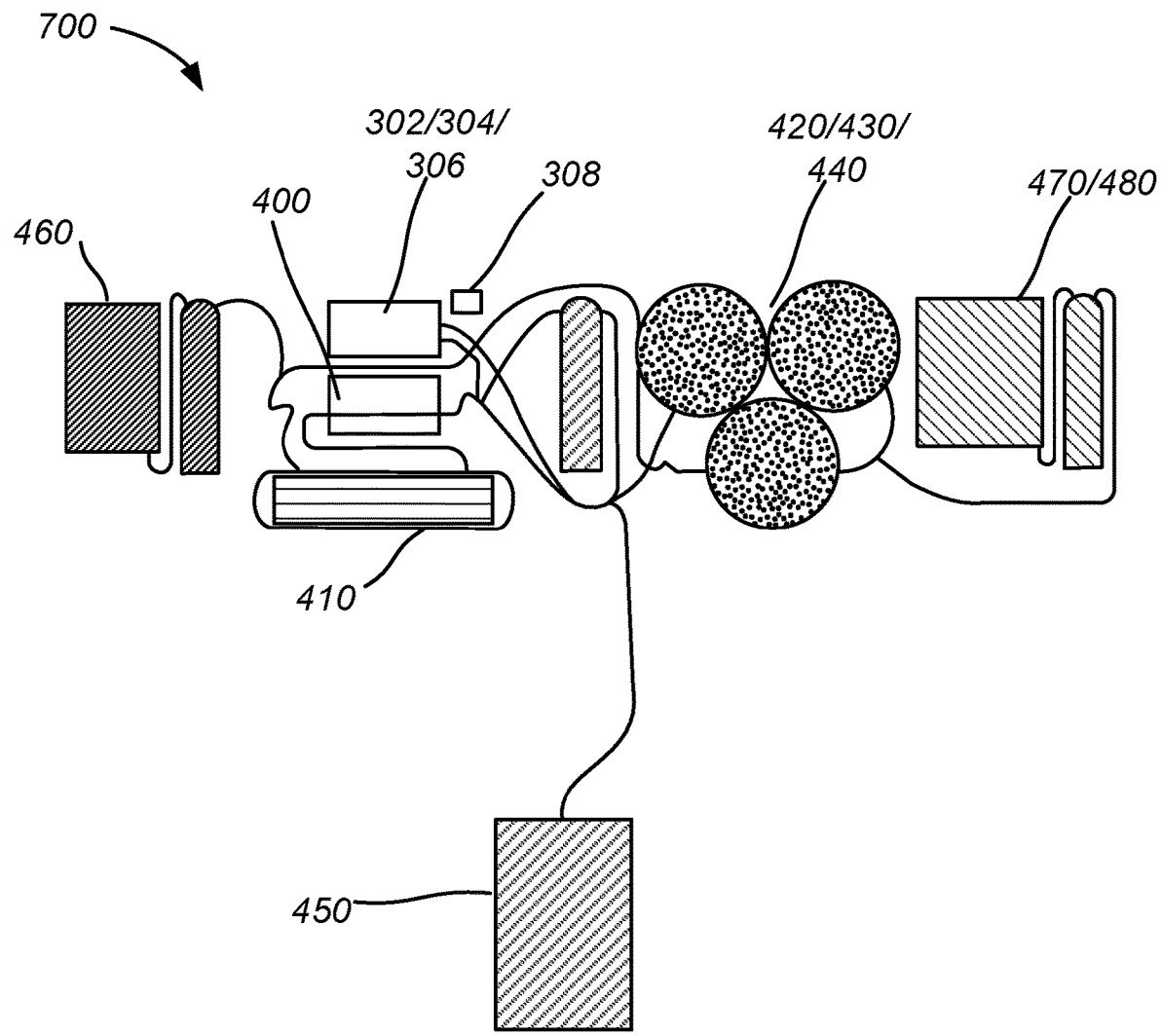
FIG. 4 is a schematic diagram of an example of a nighttime dialysis system in a configuration configured to be coupled to a support.

FIG. 4 is a schematic diagram of one non-limiting example of a nighttime dialysis system 700 configured to be coupled to a support. The nighttime dialysis system 700 can have one or more characteristics of the nighttime dialysis system 300 as described with reference to FIG. 2. As shown in FIG. 4, the nighttime dialysis system 700 can have its components, such a plurality of dialysate regenerating components (e.g. 420, 430, 440), one or more pumps (e.g. 400, 456, 466, 476), a dialyzer (e.g. 410), a blood detector (e.g. 306), a blood thinner reservoir (e.g. 460), optional electrolyte reservoirs (e.g. 470, 480, 490), an optional bubble detector (e.g. 304), an optional battery (e.g. 308), a power cord for external power (not shown), a control unit (e.g. 302) and an ultrafiltrate collector (e.g. 450), arranged in a manner to facilitate positioning of the nighttime dialysis system 700 on a support. As described herein, the nighttime dialysis system 700 can be positioned on a support, for example while the patient is sleeping, such that the patient does not transport the system 700 around. The nighttime dialysis system 700 is typically less compact than a daytime dialysis system. The nighttime dialysis system 700 is configured to perform more toxin removal functions than the daytime dialysis system. For example, the nighttime dialysis system 700 comprises more sorbent-containing cartridges to provide the additional toxin removal functions. The additional toxin removal functions for toxins such as urea, provided by the nighttime dialysis system 700, enable use of the lighter and/or more compact daytime dialysis system 600 while the patient is more mobile. It is to be understood that upon reading this disclosure, one of skill in the art will recognize that some components of the nighttime system are optional and need not be included in every configuration described herein.

As the nighttime dialysis system 700 is typically positioned on a support, instead of being worn by a patient, the nighttime dialysis system 700 is generally configured to be heavier in weight and/or larger in size. The nighttime dialysis system 700 is configured to perform the additional toxin removal functions while the patient is able to have the dialysis system 700 on a support, such that the patient can use the lighter and/or smaller daytime dialysis system 600 while the patient is typically mobile. For example, alternating use between the nighttime dialysis system 700 and the daytime dialysis system 600 provides the patient desired water and sodium removal and nitrogen balance, such as during a 24-hour period. In some embodiments, the daytime dialysis system 600 is used for about 8 to about 16 continuous hours, and the nighttime dialysis system 700 is used for about 8 to about 16 continuous hours. For example, the daytime dialysis system 600 is used for about 12 continuous hours, and the nighttime dialysis system 700 is used for about 12 continuous hours. In some embodiments, the daytime dialysis system 600 is used for about 8 continuous hours, about 10 continuous hours, about 12 continuous hours, about 14 continuous hours, or about 16 continuous hours. In some embodiments, the nighttime dialysis system 700 is used, for about 8 continuous hours, about 10 continuous hours, about 12 continuous hours, about 14 continuous hours, or about 16 continuous hours.

Figure 5:
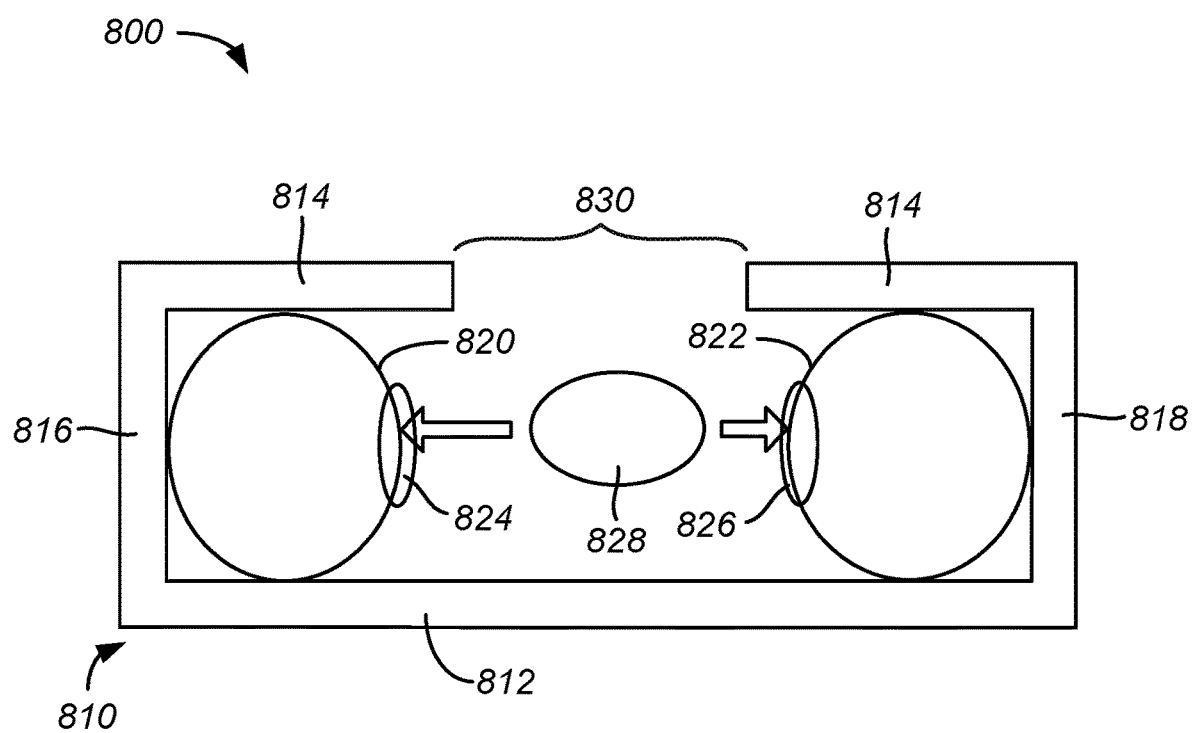
FIG. 5 is a schematic diagram of a cross-sectional view of an example of a side-to-side pulsatile pump.

In any embodiment described herein, one or more dialysis systems described herein include a dual channel, side-to-side pulsatile pump. FIG. 5 is a cross-sectional schematic view of an example of a side-to-side pulsatile pump 800. The side-to-side pulsatile pump 800 can be powered by a battery, including a rechargeable battery, and/or by an electrical wall outlet. For example, the side-to-side pulsatile pump 800 can be powered by a battery to enable transport of the pump 800, thereby facilitating transport of the dialysis system which incorporates the pump 800 (e.g., the daytime dialysis systems as described with reference to FIGS. 1 and 3). The side-to-side pulsatile pump 800 can be powered by an electrical outlet while the pump 800 is stationary, such as a pump incorporated as part of a nighttime dialysis system (e.g., the nighttime dialysis systems described with reference to FIGS. 2 and 4). Alternately, in some configurations, the rechargeable battery (e.g., the daytime dialysis systems) can be recharged when the daytime system is coupled to the nighttime system powered by an electrical wall outlet.

The side-to-side pulsatile pump 800 comprises an external casing 810 comprising a first wall 812, such as a bottom wall, a second wall 814, such as a top wall, and a third wall 816 and a fourth wall 818, such as two lateral walls. In some embodiments, the external casing 810 comprises a polymeric material, such as to provide a lighter and more mobile pump 800.

In some embodiments, the side-to-side pulsatile pump 800 is configured to retain a blood ventricle tubing 820 configured to permit the flow of blood therethrough from the patient, and a dialysate ventricle tubing 822 configured to permit flow therethrough of dialysate, within the casing 810. The side-to-side pulsatile pump 800 comprises a compression disc 828 configured to provide side-to-side motion to apply a first pressure 824 to the blood ventricle tubing 820 and a second pressure 826 to the dialysate ventricle tubing 822 in alternate fashion. For example, side-to-side motion of the compression disc 828 provides alternating compression of the blood ventricle tubing 820 and the dialysate ventricle tubing 822 against corresponding lateral walls of the external casing 810, such as against the third wall 816 and the fourth wall 818 of the external casing 810, respectively. In some embodiments, the blood ventricle tubing 820 and the dialysate ventricle tubing 822 in contact with the compression discs are reinforced, such as an increased thickness around the portions of the blood ventricle tubing 820 and the dialysate ventricle tubing 822. Reinforcement of portions of the blood ventricle tubing 820 and the dialysate ventricle tubing 822 in contact with the compression disc 828 can mitigate the risk of a ventricle rupture due to the repetitive compression by the compression disc 828.

In some embodiments, the first wall 814 comprises an opening 830. The opening 830 is configured for removal of the blood ventricle tubing 820 and/or the dialysate ventricle tubing 822 such that the tubings can be replaced easily without requiring disassembly of the pump casing/housing. The blood ventricle tubing 820 and the dialysate ventricle tubing 822 can be removed separately such that each can be changed with a different frequency. For example, the blood ventricle tubing 820 can be changed once or twice a week while the dialysate ventricle tubing 822 can be changed daily. The opening 830 is configured such that the blood ventricle tubing 820 and the dialysate ventricle tubing 822 are securely positioned within the casing 810, reducing or preventing dislodging of the blood ventricle tubing 820 and the dialysate ventricle tubing 822 from within the casing 810.

Figure 6:
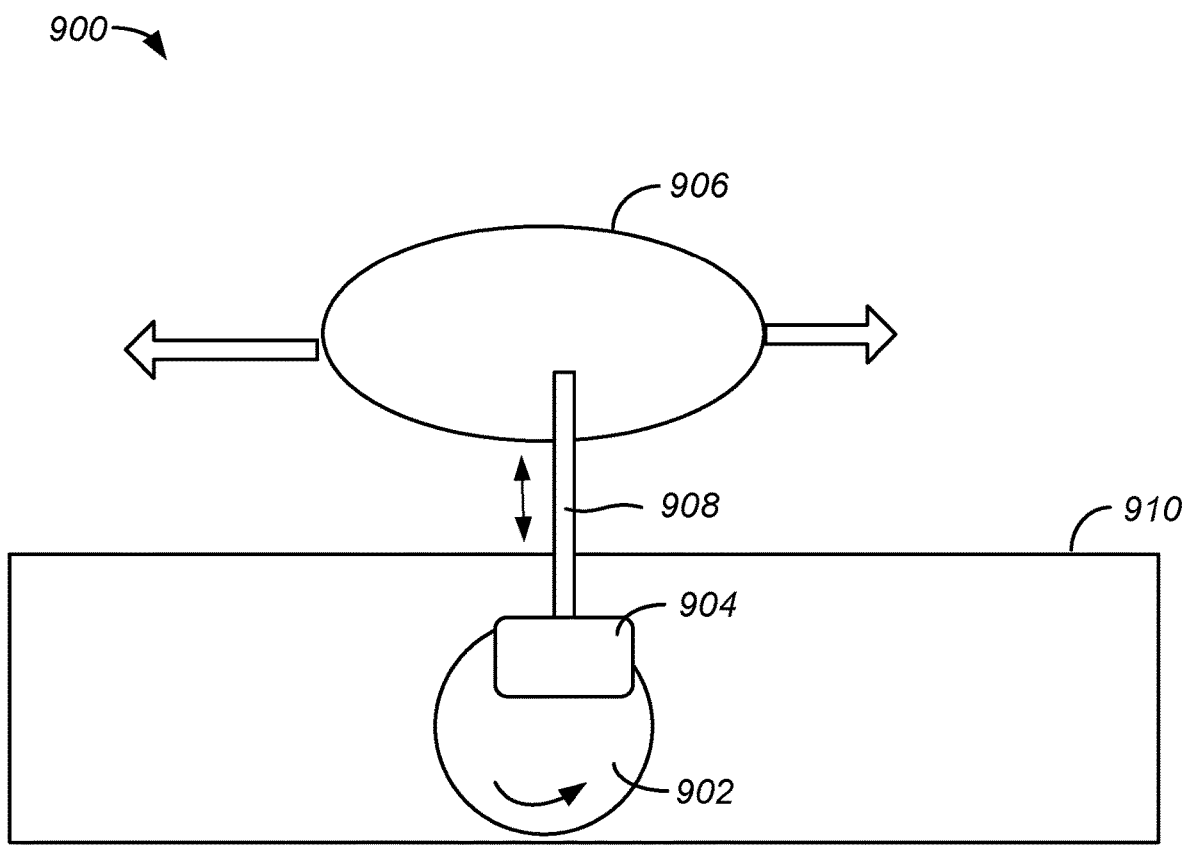
FIG. 6 is a schematic diagram of an example configuration of a motor, gear box and compression disc of a side-to-side pulsatile pump.

FIG. 6 is a schematic diagram of an example configuration of a motor 902, a gear box 904 and a compression disc 906 of a side-to-side pulsatile pump 900. The side-to-side pulsatile pump 800 of FIG. 5 comprises the configuration described with reference to FIG. 6. In some embodiments, the side-to-side pulsatile 900 includes a motor 902 coupled to a rod 908 via a gear box 904. Rotation of the motor 902 effects an up and down motion of the rod 908. Up and down motion of the rod 908 results in side-to-side motion of the compression disc 906, which in turn applies pressure to respective sides of a blood ventricle tubing and a dialysate ventricle tubing in alternate fashion, such as the blood ventricle tubing 820 and the dialysate ventricle tubing 822 described with reference to FIG. 5. In some embodiments, the motor 902 and the gear box 904 are retained in a housing 910. In some embodiments, the housing 910 comprises a polymeric materials, for example to provide a lighter pump 900, and thereby a lighter dialysis system which incorporates the pump 900.

One or more side-to-side pulsatile pumps described herein can be configured to provide desired pumping volume for both blood and dialysate, while reducing or eliminating problems associated with known pumps. In some embodiments, one or more side-to-side pulsatile pumps described herein can provide pumping volumes of greater than about 35 milliliter per minute (mL/min). In some embodiments, a dialysis system using a side-to-side pulsatile pump 900 is configured to provide a flow rate of dialysate of about 100 mL/min. For example, running such a dialysis system for about 8 continuous hours can remove up to 22 grams of urea, such as to provide desired homeostasis. For example, known pumps use a metal rocker arm that oscillates up and down to alternately compress two parallel ventricles. The up and down motion can change the position of the ventricles within the pump, and/or dislodge the ventricles, leading to adverse effects in the flow of the blood and dialysate. For example, movement and/or dislodging of the ventricles can contribute to significant pressure drop within the dialysis system and reduction in flow of blood and dialysate. Known pumps do not provide desired pumping volume, for example providing pumping volume of less than 30 mL/min. For example, pumps using the rocker arms configured for up and down motion typically provide pumping volumes of no more than about 25 mL/min to about 30 mL/min. Known pumps are configured such that the blood and dialysate ventricles are changed together, leading to more frequent changing of the dialysate ventricles.

Figure 7:
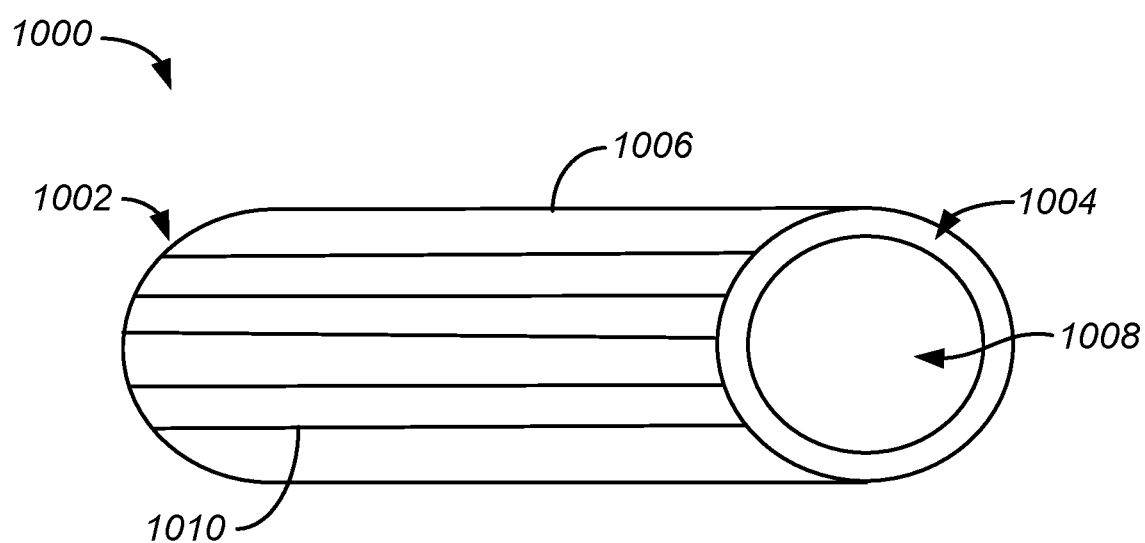
FIG. 7 is a schematic diagram of a portion of a blood tubing or dialysate tubing configured to demonstrate reduced kinking.

Optionally, in any one of the embodiments, one or more of the daytime dialysis systems and nighttime dialysis systems described herein include tubing configured to reduce or prevent kinking. FIG. 7 is a schematic diagram of a portion of a blood or dialysate tubing 1000 configured to demonstrate reduced kinking. The blood or dialysate tubing 1000 includes a first end 1002, a second end 1004 and a wall 1006 extending therebetween. The wall 1006 defines an inner lumen 1008 of the blood or dialysate tubing 1000. The wall 1006 includes a dual lumen catheter comprising a plurality of filaments embedded therewithin, the dual lumen catheter comprising 1010 embedded therein configured to provide added resistance to kinking. In some embodiments, the plurality of filaments 1010 extend along an entire length of the blood or dialysate tubing 1000. In some embodiments, the plurality of filaments 1010 extend along an entire length of the blood or dialysate tubing 1000 in a straight or spiraling circumferential manner. In some embodiments, the plurality of filaments 1010 extend along one or more portions of the blood or dialysate tubing 1000. In any one of these embodiments, the goal of the filaments is to provide an increase in rigidity to reduce or prevent kinking, while maintaining flexibility. Reduction in kinking can advantageously provide improved reliability in the flow of blood and/or dialysate through a dialysis system. In any one of these embodiments, the filaments are typically comprised of metal. In some embodiments the filaments are comprised of an electrically conductive material and configurable to provide a signal to a control unit to indicate when the tubing or the lumen becomes kinked. In some embodiments the filaments are comprised of copper. In some embodiments the filaments are comprised of nitinol (NiTi).

Figure 8:
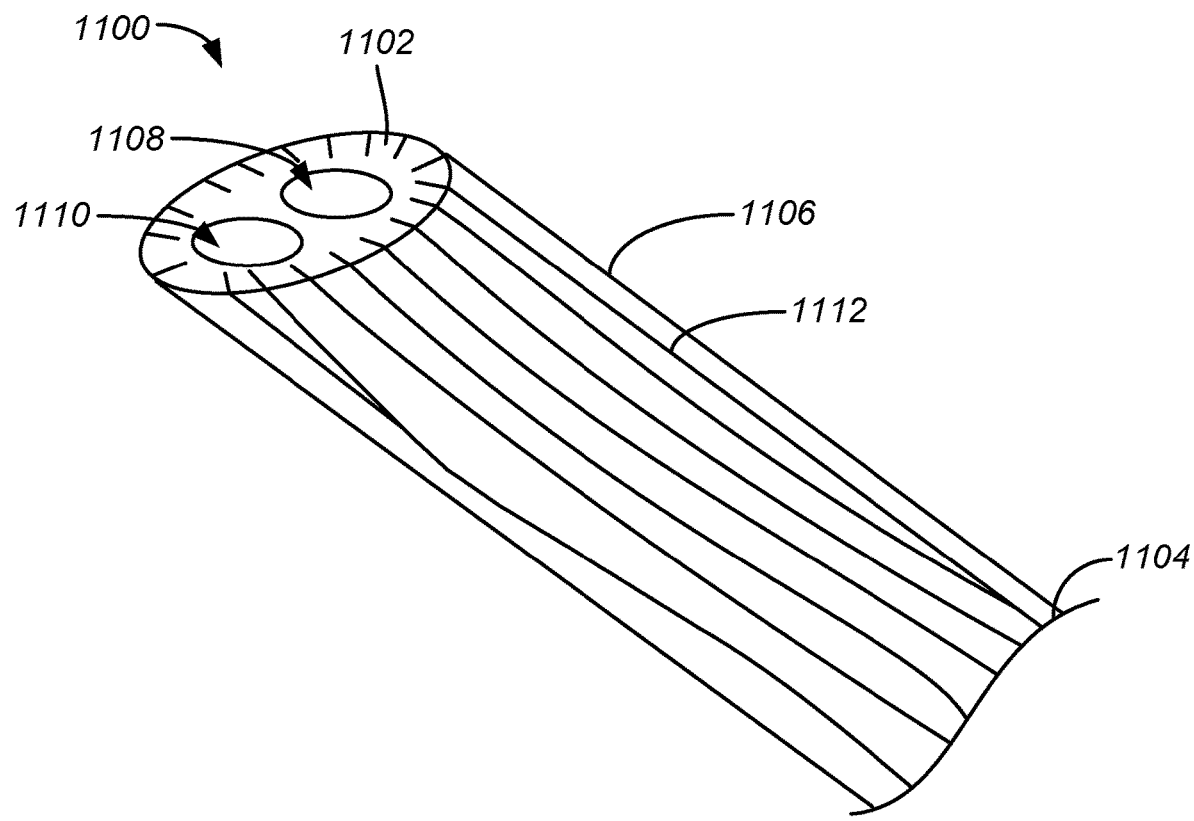
FIG. 8 is a schematic diagram of an example of a dual lumen catheter.

Optionally, FIG. 8 is a schematic diagram of a non-limiting example of a dual lumen catheter 1100 that may be used with any of the dialysis systems described herein. The dual lumen catheter 1100 includes a first end 1102, a second end 1104 and a wall 1106 extending therebetween. The wall 1106 can define two lumens, a first lumen 1108, and a second lumen 1110 therewithin, the two lumens 1108, 1110 extending parallel to one another. The dual lumen catheter 1100 comprises a plurality of filaments 1112 embedded within its wall 1106 such that the dual lumen catheter 1100 can demonstrate improved resistance to kinking. In some embodiments, the plurality of filaments 1112 can extend along an entire length of the dual lumen catheter 1100. In some embodiments, the plurality of filaments 1112 extend along an entire length of the dual lumen catheter 1100 in a straight or spiraling circumferential manner. In some embodiments, the plurality of filaments 1112 can extend along one or more portions of the dual lumen catheter 1100. In some embodiments, the dual lumen catheter 1100 can be configured to be inserted within the patient to provide blood flow from and back into the patient, for example one lumen of the catheter 1100 for providing blood flow from the patient, and the other lumen for providing blood flow back to the patient from a dialysis system. In some embodiments, the dual lumen catheter 1100 can have an extended length such that the dual lumen catheter 1100 can be inserted within the superior vena cava or the subclavian vein, and exit around the waist area of the patient such that the dual lumen catheter 1100 can be coupled to a dialysis system worn around the waist of the patient. In some embodiments, the dual lumen catheter 1100 can be used in combination with a daytime and/or nighttime dialysis system as described herein. For example, the dual lumen catheter 1100 can be configured for coupling to a daytime dialysis system coupled to a belt worn around the waist of the patient.

Figure 9A:
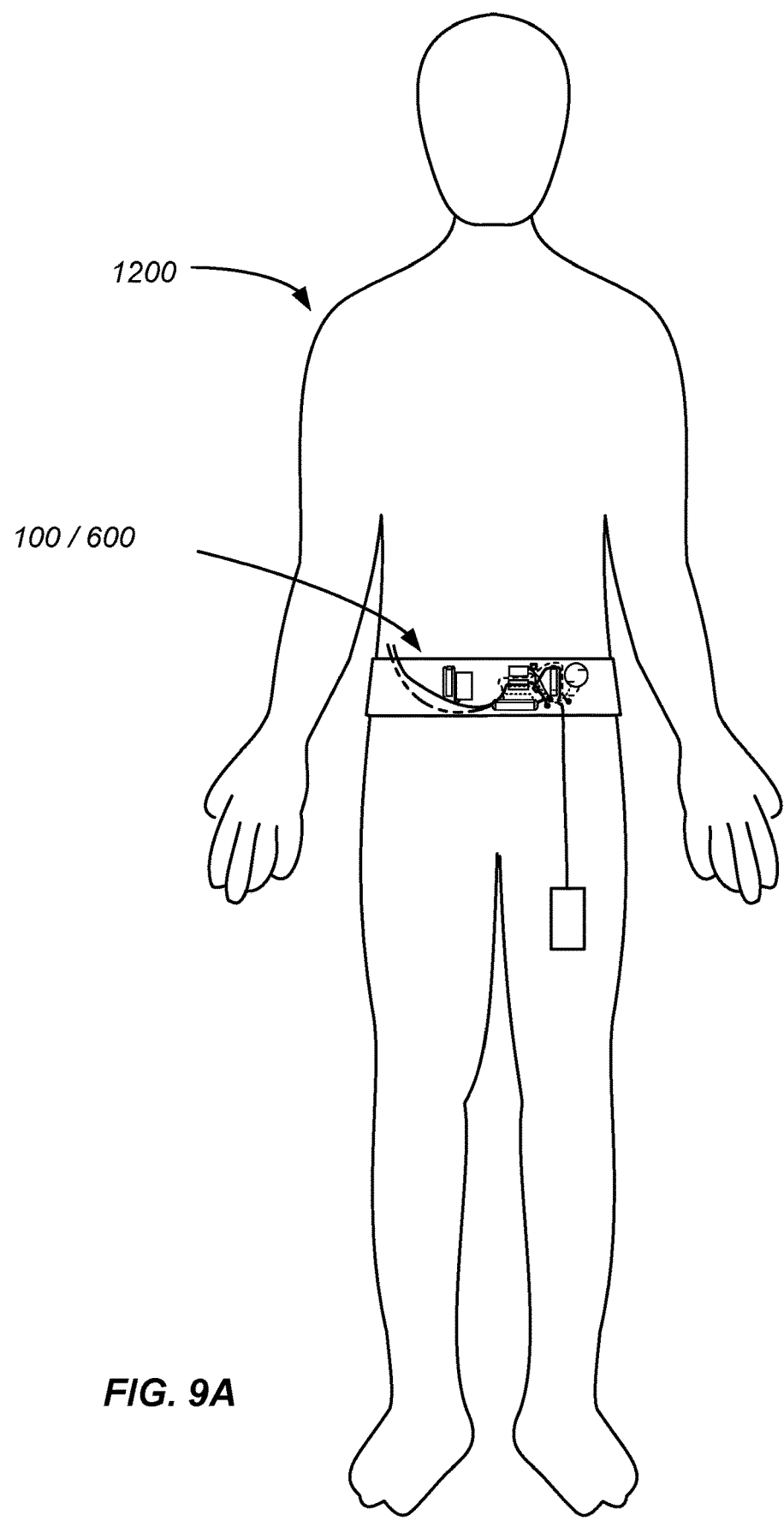
FIG. 9A is an illustrative embodiment of the wearable daytime dialysis system on a belt worn by a patient.
Figure 9B:
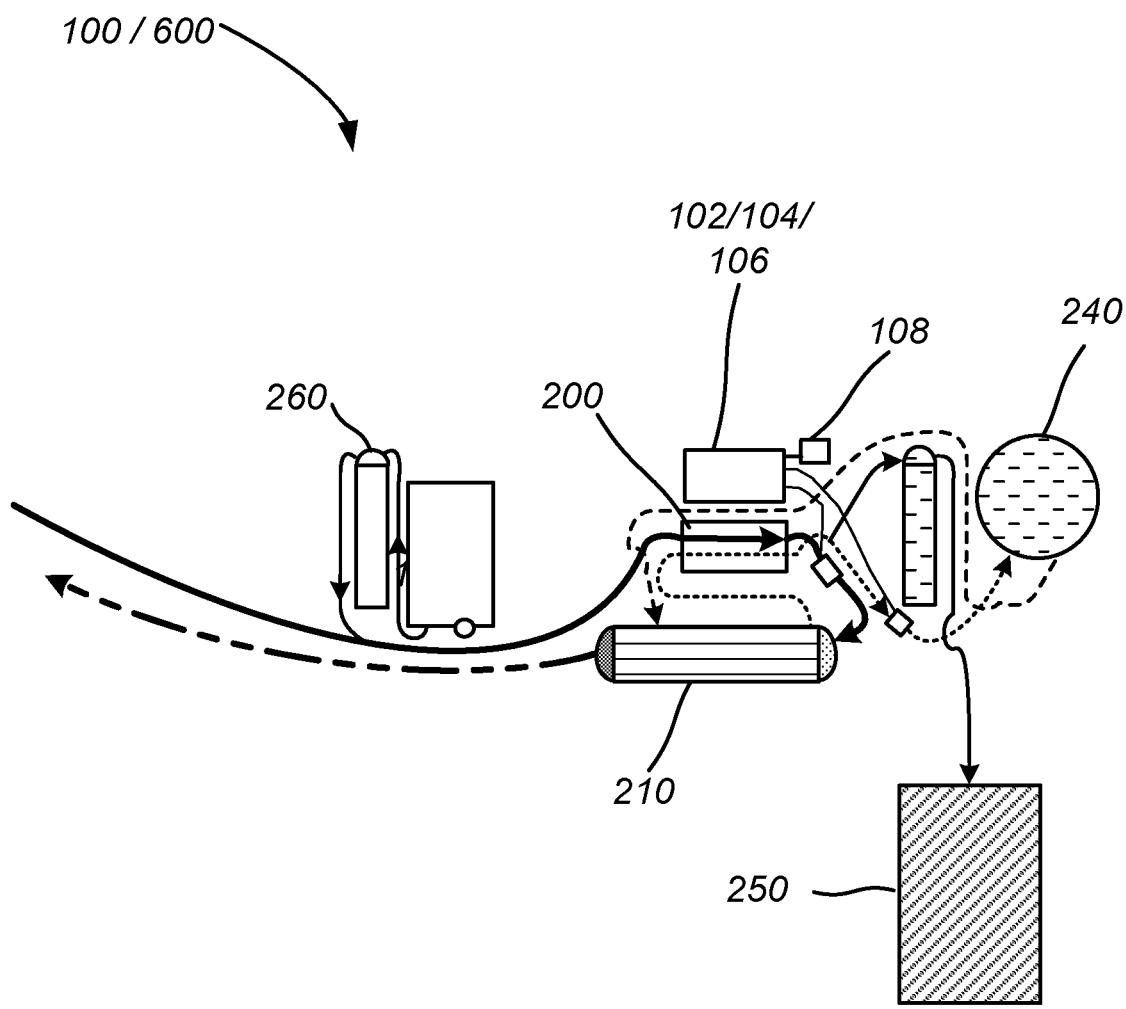
FIG. 9B is a detailed illustrative embodiment of the daytime dialysis system circuit, as illustrated in FIG. 9A.

FIG. 9A is an illustrative embodiment of the wearable daytime dialysis system 100/600 on a belt worn by a patient 1200. FIG. 9B is a detailed illustrative embodiment of the daytime dialysis system circuit, as illustrated in FIG. 9A.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A hemodialysis system comprising:
   a dialyzer;
   a blood circuit, configured to receive blood from a patient and circulate the blood through the dialyzer to remove toxins from the blood;
   a sterile dialysate circuit, configured to circulate dialysate through the dialyzer to receive the toxins removed from the blood;
   a side-to-side pulsatile pump operably coupled to the blood circuit and the dialysate circuit to simultaneously drive the blood and the dialysate therethrough, wherein the side-to-side pulsatile pump comprises a horizontal configuration for actuating the blood and the dialysate, the side-to-side pulsatile pump comprising:
      a blood ventricle tubing fluidly coupled to the blood circuit;
      a dialysate ventricle tubing fluidly coupled to the dialysate circuit, the dialysate ventricle tubing parallel the blood ventricle tubing; and
      a compression disc therebetween;
   a daytime module comprising a daytime sorbent, wherein the daytime module is integrated with the sterile dialysate circuit; and
   a nighttime module comprising one or more nighttime sorbents, wherein the nighttime module is configured to be coupled to the sterile dialysate circuit for a stationary period, wherein when the nighttime modules is coupled to the sterile dialysate circuit, the one or more nighttime sorbents replace the daytime sorbent, such that the hemodialysis system is mobile when the nighttime module is not coupled to the sterile dialysate circuit, and the hemodialysis system is stationary when the nighttime module is coupled to the sterile dialysate circuit.

2. The hemodialysis system of claim 1, wherein the side-to-side pulsatile pump is configured to allow access to one of the blood circuit and the sterile dialysate circuit without removing the other.

3. The hemodialysis system of claim 1, wherein the compression disc is configured to apply a first pressure to the blood ventricle tubing and a second pressure to the dialysate ventricle tubing in an alternating fashion.

4. The hemodialysis system of claim 1, wherein the side-to-side pulsatile pump is configured to drive the blood and dialysate through the system in countercurrent fashion.

5. The system of claim 1, wherein the daytime module is coupled to a belt configured to be worn by the patient during operation, untethered, to allow the patient to move unconstrained.

6. The system of claim 1, wherein the nighttime module removes additional toxins from the blood, not accounted for by the daytime module.

7. The system of claim 1, wherein the daytime module further comprises:
   a battery;
   a rechargeable battery; or
   a combination thereof.

8. The system of claim 1, further comprising
   an ultrafiltrate collector operably coupled to the sterile dialysate circuit downstream of the side-tip-side pulsatile pump to continuously remove excess fluid from the sterile dialysate circuit.

9. The system of claim 1, further comprising a pH sensor to test for a change in ammonia in the system.

10. The system of claim 1, wherein the daytime sorbent and the nighttime sorbents comprise at least one of zirconium phosphate; hydrous zirconium oxide; metals containing zirconium; alloys containing zirconium; an organic compound containing zirconium; an inorganic compound containing zirconium; minerals containing zirconium; urease, or combinations thereof.

11. The system of claim 1, wherein the daytime module is configured for:
   about 8 hours of continuous use;
   about 10 hours of continuous use;
   about 12 hours of continuous use;
   about 14 hours of continuous use; or about 16 hours of continuous use;
during a first portion of a combined cycle within a 24 hour period.

12. The system of claim 1, further comprising a blood thinner reservoir operably coupled to the blood circuit to supply blood thinner thereto.

13. The system of claim 12, wherein the blood thinner reservoir comprises at least one of heparin or a blood thinning agent.

14. The system of claim 1, further comprising one or more electrolyte reservoirs operably coupled to the sterile dialysate circuit to supplement the dialysate flow with electrolytes.

15. The system of claim 14, wherein the one or more electrolyte reservoirs comprise sodium bicarbonate, magnesium, or, calcium.

* * * * *

UNITED STATES PATENT AND TRADEMARK OFFICE
CERTIFICATE OF CORRECTION

PATENT NO. : 10,933,183 B2
APPLICATION NO. : 15/890718
DATED : March 2, 2021
INVENTOR(S) : Victor Gura Page 1 of 1

It is certified that error appears in the above-identified patent and that said Letters Patent is hereby corrected as shown below:

In the Claims

In Column 28, Line 48, in Claim 8, delete "comprising" and insert --comprising:-- therefor In Column 28, Line 50, in Claim 8, delete "side-tip-side" and insert --side-to-side-- therefor Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*